United States Patent
Mpofu et al.

(10) Patent No.: US 11,278,618 B2
(45) Date of Patent: *Mar. 22, 2022

(54) USE OF IL-17 ANTAGONISTS TO INHIBIT THE PROGRESSION OF STRUCTURAL DAMAGE IN PSORIATIC ARTHRITIS PATIENTS

(71) Applicant: Novartis AG, Basel (CH)

(72) Inventors: Shephard Mpofu, Oberwil (CH); Hanno Richards, Therwil (CH); Gregory Ligozio, Basking Ridge, NJ (US)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/508,441

(22) PCT Filed: Sep. 8, 2015

(86) PCT No.: PCT/IB2015/056871
§ 371 (c)(1),
(2) Date: Mar. 2, 2017

(87) PCT Pub. No.: WO2016/038538
PCT Pub. Date: Mar. 17, 2016

(65) Prior Publication Data
US 2017/0281762 A1    Oct. 5, 2017

Related U.S. Application Data

(60) Provisional application No. 62/048,512, filed on Sep. 10, 2014.

(51) Int. Cl.
| | |
|---|---|
| *A61K 39/395* | (2006.01) |
| *C07K 16/24* | (2006.01) |
| *A61K 39/00* | (2006.01) |
| *C07K 16/18* | (2006.01) |
| *A61K 45/00* | (2006.01) |

(52) U.S. Cl.
CPC .......... *A61K 39/3955* (2013.01); *A61K 39/00* (2013.01); *C07K 16/18* (2013.01); *C07K 16/244* (2013.01); *A61K 45/00* (2013.01); *A61K 2039/505* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 9,717,791 B2* | 8/2017 | Guettner | A61K 39/3955 |
| 2013/0202610 A1* | 8/2013 | Guettner | A61K 39/3955 |
| | | | 424/139.1 |
| 2013/0209480 A1* | 8/2013 | Mpofu | A61K 31/519 |
| | | | 424/142.1 |
| 2018/0008706 A1* | 1/2018 | Mpofu | A61K 45/06 |

FOREIGN PATENT DOCUMENTS

| | | | |
|---|---|---|---|
| WO | WO 2006/013107 A1 | 2/2006 | |
| WO | WO 2012/045848 A1 | 4/2012 | |
| WO | WO-2012059598 A2 * | 5/2012 | ........... A61K 31/519 |
| WO | WO 2012/082573 A1 | 6/2012 | |
| WO | WO 2013/077907 A1 | 5/2013 | |

OTHER PUBLICATIONS

Langley et al (N Engl J Med 2014;371:326-38) (Year: 2014).*
Baron-Faust, "The IL-17 Superfamily: What Future for PsA?", Rheumatology Network, Mar. 18, 2014, retrieved from the internet: http://www.rheumatologynetwork.com/psoriatic-arthritis/il-17-superfamily-what-future-psa, Mar. 18, 2014.
Weitz et al., "Ustekinumad: targeting the IL-17 pathway to improve outcomes in psoriatic arthritis", Expert Opinion on Biological Therapy, 2014, vol. 14, No. 4, pp. 515-526, 2014.
Patel et al., "Effect of IL-17A blockade with secukinumad in autoimmune diseases", Annals of the Rheumatic Diseases, 2013, vol. 72, Supp. 2, ii116-ii123, 2013.
Gaffen et al., "IL-23-IL-17 immune axis: Discovery, Mechanistic Understanding, and Clinical Testing", Nature Reviews Immunology, 2014, vol. 14, No. 9, pp. 585-600, 2014.
Gottlieb et al., "AB0738—Secukinumab Reduces HSCRP Levels in Subjects with Moderate-to-Severe Plaque Psoriasis and Concomitant Psoriatic Arthritis: A Sub-Analysis from the Phase 3 Erasure Study", Annals of the Rheumatic Diseases, 2014, pp. 1047-1048.
Gottlieb eta l., "Secukinumab Shows Substantial Improvement in Both Psoriasis Symptoms and Physical Functioning in Moderate-to-Severe Psoriasis Patients with Psoriatic Arthritis: A Subanalysis of a Phase 3, Multicenter, Double-Blind, Placebo-Controlled Study", American Colleage of Rheumatology Metting Abstracts, Jan. 1, 2013, AB No. 319, 2013.
Mcinnes et al., "Anti-Interleukin 17A Monoclonal Antibody Secukinumab Reduces Signs and Symptoms of Psoriatic Arthritis in a 24-Week Multicenter, Double-Blind, Randomized, Placebo-Controlled Trial", American College of Rheumatology Meeting Abstracts, Jan. 1, 2011, AB No. 779, 2011.
Chandran et al., "Reappraisal of the Effectiveness of Methotrexate in Psoriatic Arthritis: Results from a Longitudinal Observational Cohort", J Rheumatol, 35;469-471, 2008.
Kavanaugh et al., "The Infliximab Multinational Psoriatic Arthritis Controlled Trial (IMPACT): results of radiographic analyses after 1 year", Ann Rheum Dis, 65:1038-1043, 2006.
Kavanaugh et al., "Clinical efficacy, radiographic and safety findings through 2 years of golimumab treatment in patients with active psoriatic arthritis: results from a long-term extension of the randomised, placebo-controlled GO-REVEAL study", Ann Rheum Dis, 72:1777-1785, 2013.

(Continued)

*Primary Examiner* — Brian Gangle
*Assistant Examiner* — Andrea K McCollum
(74) *Attorney, Agent, or Firm* — David Goetz

(57) ABSTRACT

The present disclosure relates to methods, uses, medicaments, pharmaceutical formulations, dosage forms, and kits for inhibiting the progression of structural damage in psoriatic arthritis (PsA) patients using Interleukin-17 (IL-17) antagonists, e.g., IL-17 antibodies and antigen-binding fragments thereof, e.g., secukinumab.

22 Claims, 15 Drawing Sheets
Specification includes a Sequence Listing.

(56) References Cited

OTHER PUBLICATIONS

Heijde et al., "Effect of different imputation approaches on the evaluation of radiographic progression in patients with psoriatic arthritis: results of the RAPID-PsA 24-week phase III double-blind randomised placebo-controlled study of certolizumab pegol", Ann Rheum Dis, 73:233-237, 2014.

Kavanaugh et al., "Ustekinumab, an anti-IL-12/23 p40 monoclonal antibody, inhibits radiographic progression in patients with active psoriatic arthritis: results of an integrated analysis of radiographic data from the phase 3, multicentre, randomised, double-blind, placebo-controlled PSUMMIT-1 and PSUMMIT-2 trials", Ann Rheum Dis, 73:1000-1006, 2014.

Mease et al., "Brodalumab, an Anti-IL17RA Monoclonal Antibody, in Psoriatic Arthritis", N Engl J Med, 370:2295-306, 2014.

D van der Heijde et al., "Psoriatic arthritis imaging: a review of scoring methods", Ann Rheum Dis, 64(Suppl II):ii61-ii64, 2005.

Mease & McInnes, "Secukinumab: A New Treatment Option for Psoriatic Arthritis", Rheumatol Ther, (2016), 3:5-29.

Goulabchand et al., "Effect of tumour necrosis factor blockers on radiographic progression of psoriatic arthritis: a systematic review and meta-analysis of randomised controlled trials", Ann Rheum Dis, 2014;73:414-419.

Fagerli et al. Ann, "Switching between TNF inhibitors in psoriatic arthritis: data from the NOR-DMARD study", Rheum Dis, 2013;72:1840-1844.

Mantravadi et al., (2017) "Tumor necrosis factor inhibitors in psoriatic arthritis", Expert Review of Clinical Pharmacology, 10:8, 899-910.

Mease & Armstrong, "Managing Patients with Psoriatic Disease: The Diagnosis and Pharmacologic Treatment of Psoriatic Arthritis in Patients with Psoriasis", Drugs, (2014), 74:423-441.

McKee, "Novartis' Cosentyx shown to inhibit joint damage in PsA", Downloaded at http://www.pharmatimes.com/news/novartis_cosentyx_shown_to_inhibit_joint_damage_in_psa_1210758 on Dec. 19, 2017.

Weselman, "Psoriatic Arthritis", American College of Rheumatology, 2018; updated Mar. 2017. Available at: https://www.rheumatology.org/I-Am-A/Patient-Caregiver/Diseases-Conditions/Psoriatic-Arthritis.

Novartis Pharmaceuticals UK Ltd., UK Summary of Product Characteristics for Cosentyx®, Updated Sep. 1, 2017, Novartis Pharmaceuticals UK Ltd., available at: https://www.medicines.org.uk/emc/product/3669/smpc/print.

US Highlights of Prescribing Information for Stelara®, revised Sep. 2016, Janssen Biotech, Inc. available at: https://www.accessdata.fda.gov/drugsatfda_docs/label/2016/761044lbl.pdf.

Mrowietz et al., "Definition of treatment goals for moderate to severe psoriasis: a European consensus", Archives for Dermatological Research, 2011, vol. 303(1):1-10.

Mease et al., "Subcutaneous Secukinumab Inhibits Radiographic Progression in Psoriatic Arthritis: Primary Results from a Large Randomized, Controlled, Double-Blind Phase 3 Study", Poster presented at: American College of Rheumatology Annual Meeting (ACR), Nov. 3-8, 2017, Abstract No. 17L.

Kunder E.V., "Lechenie psoriaticheskogo artrita", Meditsinskie novosti, 2013, N6, str.34-42 (English Abstract).

Mease P, SP0147 Non-anti-TNF biologies in PSA, Annals of the Rheumatic Diseases, 2013, vol. 71, Suppl. 3, p. 36.

\* cited by examiner

Figure 2.
A
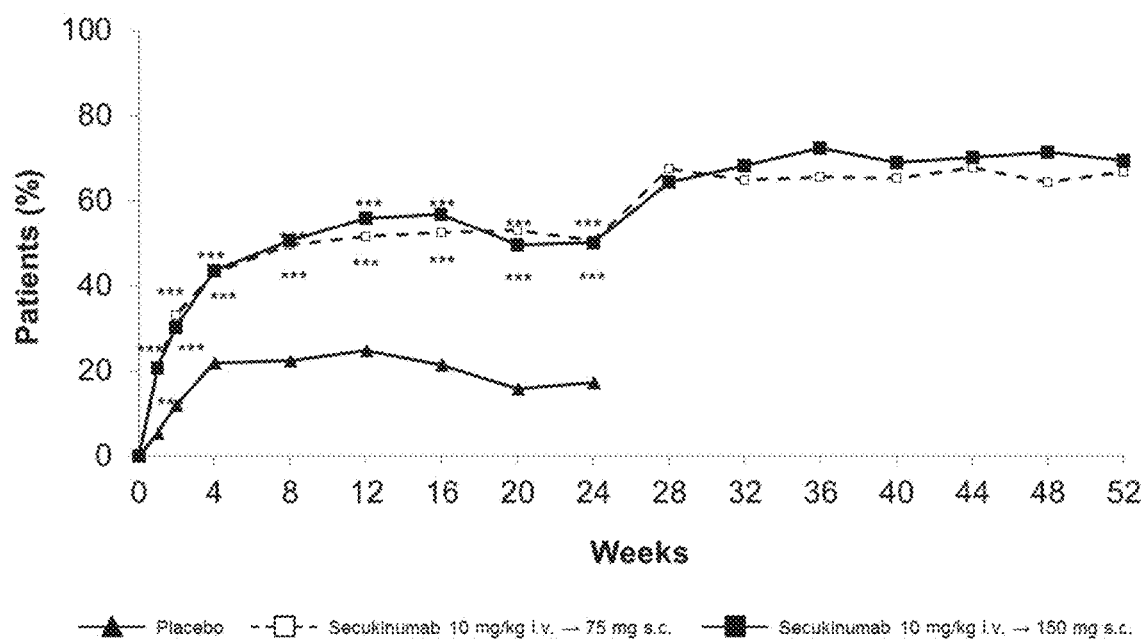
B
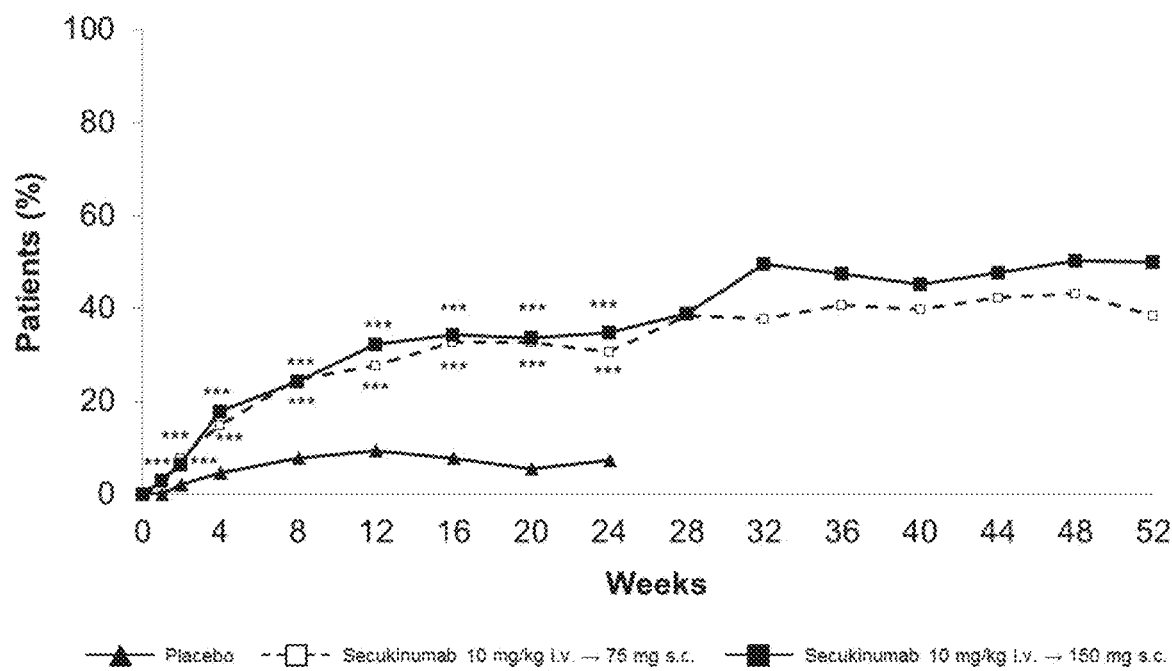

Figure 3.
A
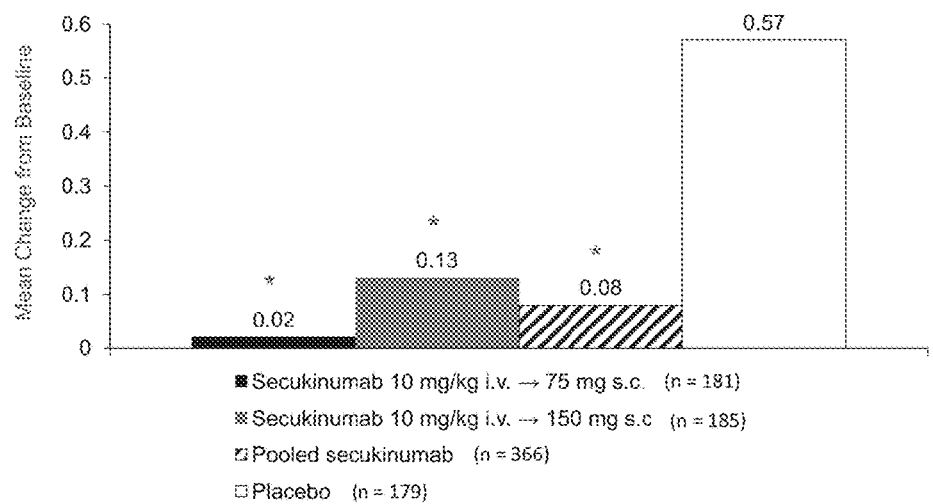
B
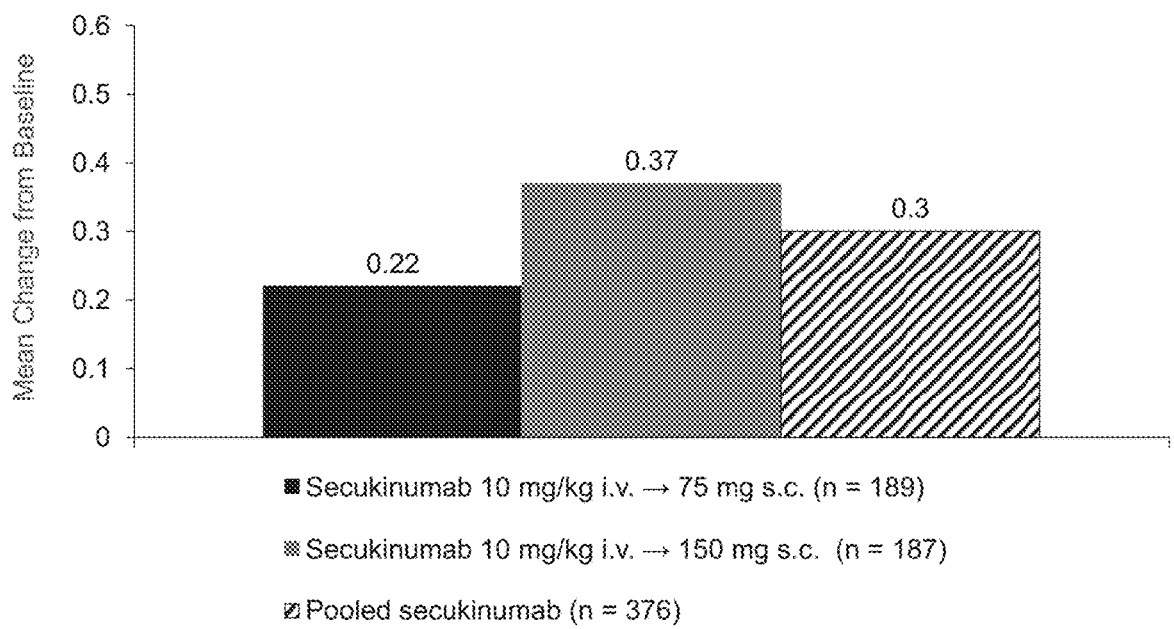

A

A

Figure 7. Cumulative Distribution Plot for week 24 total vdH-S score

USE OF IL-17 ANTAGONISTS TO INHIBIT THE PROGRESSION OF STRUCTURAL DAMAGE IN PSORIATIC ARTHRITIS PATIENTS

This disclosure claims priority to U.S. Provisional Patent Application No. 62/048,512 filed Sep. 10, 2014, the disclosure of which is incorporated by reference herein in its entirety.

TECHNICAL FIELD

The present disclosure relates to methods for inhibiting the progression of structural damage in psoriatic arthritis (PsA) patients (e.g., patients previously treated with biologicals, e.g., TNF alpha inhibitors, and patients not previously treated with biologicals) using IL-17 antagonists, e.g., secukinumab.

BACKGROUND OF THE DISCLOSURE

PsA is a chronic, systemic inflammatory disease affecting peripheral joints, connective tissues and the axial skeleton, and may be associated with psoriasis of the skin and nails (Boehncke and Menter (2013), Am J Clin Dermatol; 14:377-88; Gladman et al. (2005) Ann Rheum Dis.; 64 (Suppl 2):ii14-17). PsA is a multifaceted disease, including synovitis, enthesitis, dactylitis, spondylitis, uveitis and inflammatory bowel disease. Traditional disease modifying anti-rheumatic drugs (DMARDs) include methotrexate (MTX), sulfasalazine, cyclopsorine, and leflunomide and are inadequate for a number of patients because these drugs only partially control established disease (Mease P J (2008) Psoriatic Arthritis. In: Klippel et al, eds. Primer on Rheumatic Diseases. 13th ed. New York: Springer Science, p. 170-192). Tumor necrosis factor (TNF) inhibitors have improved the management of PsA in recent years (Mease (2013) Curr Opin Rheumatol.; 25:287-96; Mease and Armstrong (2014) Drugs 2014a; 74:423-41; Gossec et al. (2012) Ann Rheum Dis; 71:4-12; Menter et al. (2011) J Am Acad Dermatol 2011; 65:137-74), but not all patients respond to or tolerate these agents (i.e., about 40% of PsA patients) and many continue to experience significant impairment of physical function, disability and reduced quality of life (Boehncke and Menter (2013) Am J Clin Dermatol 2013; 14:377-88; Gladman et al. (2005) Ann Rheum Dis.; 64 (Suppl 2):ii14-17).

Approximately two-thirds of patients with PsA experience progressive and irreversible structural damage (e.g., erosions, joint space narrowing (JSN), osteolysis, ankylosis, etc.) associated with varying degrees of disability. Within 2 years of onset of PsA, almost 50% of patients manifest≥1 erosion and after 10 years of follow-up 55% develop≥5 deformed joints (Kavanaugh et al (2014) Ann. Rheum. Dis. 73:1000-1006). While some therapies have been shown to prevent structural damage in TNF naïve patients (e.g., ustekinumab, see Kavanaugh et al. (2014), supra), currently, there is no biological that prevents the progression of structural damage in PsA patients having prior TNF exposure (i.e., TNF inadequate responders [TNF-IR]).

SUMMARY OF THE DISCLOSURE

In light of the above, there is a need to develop new therapies that inhibit the progression of structural damage associated with PsA, particularly for PsA patients who are TNF-IR.

A growing body of evidence implicates interleukin-17A in the pathogenesis of PsA. Increased levels of interleukin-17A-producing cells are found in the circulation and joints and psoriatic skin plaques of patients (Jandus (2008) Arthritis Rheum; 58:2307-17; Kagami (2010) J Invest Dermatol; 130:1373-83; Lin (2011) J Immunol; 187:490-500; Noordenbos (2012) Arthritis Rheum; 64:99-109), and have been shown to correlate with measures of disease activity and structural damage (Menon et al. (2014) Arthritis Rheumatol.; 66:1272-81). Moreover, phase 2 studies have demonstrated that inhibiting the interleukin-17A ligand (McInnes et al. (2014) Ann Rheum Dis 2014; 73:349-56) or receptor (Mease et al. (2014) N Engl J Med; 370:2295-306) improves signs and symptoms of PsA, although the effect of interleukin-17A inhibition on structural damage has not previously been shown.

Secukinumab (AIN457) is a high-affinity fully human monoclonal anti-human antibody that inhibits Interleukin-17A activity. In a recent PsA proof-of-concept (PoC) study (AIN457A2206) (Example 1), secukinumab did not meet its primary efficacy endpoint (proportion of ACR20 responders at week 6 in active vs. placebo). However, larger studies, using an improved dosing regimen (Example 2), now show that secukinumab is highly effective in the treating both the signs and symptoms of PsA. Moreover, radiographic data (Examples 3-4) indicates that secukinumab is the first biological to show significant inhibition of the progression of structural damage in PsA patients regardless of prior TNF inhibitor therapy status (TNF-naïve versus prior TNF treatment) or concomitant methotrexate administration. To our knowledge, secukinumab is the first biological to exhibit inhibition of progression of structural damage in PsA patients who have been previously treated with a TNF alpha antagonist (e.g., TNF-IR patients). For example, PsA trials with ustekinumab, an antagonistic anti-IL-12/23 p40 monoclonal antibody, did not show inhibition of radiographic progression of joint damage in patients having prior TNF alpha antagonist exposure. Because IL-23 induces the differentiation of naive CD4(+) T cells into highly pathogenic helper T cells (Th17/Th(IL-17)) that produce IL-17, the fact that secukinumab inhibits radiographic progression of joint damage in patients having prior TNF alpha antagonist exposure whereas ustekinumab did not, is unexpected.

Accordingly, disclosed herein are methods of inhibiting the progression of structural damage in a PsA patient, comprising administering an IL-17 antagonist to a patient in need thereof. Also disclosed herein are methods of reducing signs and symptoms of active PsA in a PsA patient, inhibiting the progression of structural (e.g., bone and/or joint) damage in a PsA patient, and/or improving physical function in a PsA patient, comprising administering an IL-17 antagonist to a patient in need thereof. In some embodiments of the disclosed uses, methods and kits, the patient is biologic-naïve. In some embodiments of the disclosed uses, methods and kits, the patient is biologic-experienced. In some embodiments of the disclosed uses, methods and kits, the patient has not previously been treated with a TNF alpha antagonist. In some embodiments of the disclosed uses, methods and kits, the patient has previously been treated with a TNF alpha antagonist. In some embodiments of the disclosed uses, methods and kits, the patient had an inadequate response to the previous treatment with the TNF alpha antagonist (TNF-inadequate responder (TNF-IR)). In some embodiments of the disclosed uses, methods and kits, inhibition of the progression of structural damage is measured by the van der Heijde psoriatic arthritis-modified total Sharp score (mTSS). In some embodiments of the disclosed uses, methods and kits, inhibition of the progression of structural damage is measured by erosion and joint space narrowing (JSN) scores. In some embodiments of the disclosed uses, methods and kits, progression of erosion, joint space narrowing, pencil-in-cup phenomena, joint widening, joint narrowing, subluxation, bony proliferation, osteolysis, and/or ankylosis is inhibited. In some embodiments, the disclosed methods further comprise administering the patient a DMARD, e.g., methotrexate (MTX). In some embodiments of the disclosed uses, methods and kits, the IL-17 antagonist is administered to the patient intravenously (i.v.) at about 10 mg/kg every other week during week 0, 2, and 4 and thereafter is administered to the patient subcutaneously (s.c.) at about 75 mg, about 150 mg, or about 300 mg monthly (every 4 weeks), beginning during week 8. In some embodiments of the disclosed uses, methods and kits, the IL-17 antagonist is administered to the patient s.c. at about 75 mg, about 150 mg, or about 300 mg weekly during weeks 0, 1, 2, and 3, and thereafter is administered to the patient s.c. at about 75 mg, about 150 mg or about 300 mg monthly (every 4 weeks), beginning during week 4. In some embodiments of the disclosed uses, methods and kits, the patient has concomitant psoriasis (e.g., concomitant moderate to severe plaque-type psoriasis). In some embodiments of the disclosed uses, methods and kits, inhibiting the progression of structural damage is defined as a change from baseline in mTSS ≤0.5. In some embodiments of the disclosed uses, methods and kits, inhibiting the progression of structural damage is defined as a change from baseline in erosion score of ≤0.3. In some embodiments of the disclosed uses, methods and kits, inhibiting the progression of structural damage is defined as a change from baseline in JSN score of ≤0.2. In some embodiments of the disclosed uses, methods and kits, the patient is selected for treatment based on the patient having previously been administered a TNF alpha antagonist. In some embodiments of the disclosed uses, methods and kits, the IL-17 antibody, e.g., secukinumab, is administered as a liquid pharmaceutical composition (e.g., reconstituted from a lyophilisate or not reconstituted from a lyophilisate, preferably not reconstituted from a lyophilisate).

In some embodiments of the disclosed uses, methods and kits, the IL-17 antagonist is an IL-17 antibody or antigen-binding fragment thereof. In some embodiments of the disclosed uses, methods and kits, the IL-17 antibody or antigen-binding fragment thereof is selected from the group consisting of: a) an IL-17 antibody or antigen-binding fragment thereof that binds to an epitope of IL-17 comprising Leu74, Tyr85, His86, Met87, Asn88, Val124, Thr125, Pro126, Ile127, Val128, His129; b) an IL-17 antibody or antigen-binding fragment thereof that binds to an epitope of IL-17 comprising Tyr43, Tyr44, Arg46, Ala79, Asp80; c) an IL-17 antibody or antigen-binding fragment thereof that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain; d) an IL-17 antibody or antigen-binding fragment thereof that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain, wherein the IL-17 antibody or antigen-binding fragment thereof has a $K_D$ of about 100-200 pM, and wherein the IL-17 antibody or antigen-binding fragment thereof has an in vivo half-life of about 23 to about 35 days; and e) an IL-17 antibody or antigen-binding fragment thereof comprising: i) an immunoglobulin heavy chain variable domain ($V_H$) comprising the amino acid sequence set forth as SEQ ID NO:8; ii) an immunoglobulin light chain variable domain ($V_L$) comprising the amino acid sequence set forth as SEQ ID NO:10; iii) an immunoglobulin $V_H$ domain comprising the amino acid sequence set forth as SEQ ID NO:8 and an immunoglobulin $V_L$ domain comprising the amino acid sequence set forth as SEQ ID NO:10; iv) an immunoglobulin $V_H$ domain comprising the hypervariable regions set forth as SEQ ID NO:1, SEQ ID NO:2, and SEQ ID NO:3; v) an immunoglobulin $V_L$ domain comprising the hypervariable regions set forth as SEQ ID NO:4, SEQ ID NO:5 and SEQ ID NO:6; vi) an immunoglobulin $V_H$ domain comprising the hypervariable regions set forth as SEQ ID NO:11, SEQ ID NO:12 and SEQ ID NO:13; vii) an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6; viii) an immunoglobulin $V_H$ domain comprising the hypervariable regions set forth as SEQ ID NO:11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6; ix) an immunoglobulin light chain comprising the amino acid sequence set forth as SEQ ID NO:14; x) an immunoglobulin heavy chain comprising the amino acid sequence set forth as SEQ ID NO:15; or xi) an immunoglobulin light chain comprising the amino acid sequence set forth as SEQ ID NO:14 and an immunoglobulin heavy chain comprising the amino acid sequence set forth as SEQ ID NO:15. In some embodiments of the disclosed uses, methods and kits, the IL-17 antibody or antigen-binding fragment thereof is secukinumab.

Additionally disclosed herein are methods of inhibiting the progression of structural damage in a PsA patient, comprising administering to the patient about 75 mg-about 300 mg secukinumab (e.g., about 150 mg-about 300 mg, e.g., about 75 mg, about 150 mg, about 300 mg) monthly, wherein the patient has previously been treated with a TNF alpha antagonist.

Additionally disclosed herein are methods of inhibiting the progression of structural damage in a PsA patient, comprising administering to the patient about 75 mg-about 300 mg (e.g., about 150 mg-about 300 mg, e.g., about 75 mg, about 150 mg, about 300 mg) secukinumab monthly, wherein the patient has previously been treated with a TNF alpha antagonist.

Additionally disclosed herein are methods of inhibiting the progression of structural damage in a PsA patient, comprising administering to the patient about 75 mg-about 300 mg (e.g., about 150 mg-about 300 mg, e.g., about 75 mg, about 150 mg, about 300 mg) secukinumab monthly, wherein the patient is selected for treatment based on having previously been treated with a TNF alpha antagonist.

Additionally disclosed herein are methods of inhibiting the progression of structural damage in a PsA patient, comprising selectively administering to the patient about 75 mg-about 300 mg (e.g., about 150 mg-about 300 mg, e.g., about 75 mg, about 150 mg, about 300 mg) secukinumab monthly based on the patient having previously been treated with a TNF alpha antagonist.

Additionally disclosed herein are methods of inhibiting the progression of structural damage in a PsA patient, comprising administering to the patient about 150 mg or about 300 mg (e.g., about 150 mg-about 300 mg, e.g., about 75 mg, about 150 mg, about 300 mg) secukinumab by subcutaneous injection, with initial dosing at weeks 0, 1, 2, and 3, followed by monthly dosing starting at week 4. In some embodiments, the patient has previously been treated with a TNF alpha antagonist.

Additionally disclosed herein are methods of inhibiting the progression of structural damage in a PsA patient, comprising administering to the patient about 10 mg/kg secukinumab by intravenous injection at weeks 0, 2, and 4, and thereafter administering to the patient about 150 mg or about 300 mg secukinumab by subcutaneous injection starting at week 8. In some embodiments, the patient has previously been treated with a TNF alpha antagonist.

BRIEF DESCRIPTION OF THE FIGURES

FIG. 2A-C. American College of Rheumatology (ACR) responses over time from baseline to week 24 (Placebo-controlled Phase), and through Week 52 for subjects randomized to secukinumab at baseline. The proportion of subjects with a 20% (FIG. 2A), 50% (FIG. 2B) and 70% (FIG. 2C) improvement in ACR response criteria (ACR 20, ACR 50 and ACR 70, respectively) over time is shown. Missing data were imputed as nonresponses through Week 24; observed data are reported from Week 24 to Week 52. *P<0.05, P<0.01, and *P<0.001 versus placebo.

FIG. 3A-B. Mean change from baseline in modified total sharp score (vdH-mTSS) through week 24 (Placebo-controlled Phase), and through Week 52 for subjects randomized to secukinumab at baseline. The mean change from baseline in vdH-mTSS at Week 24 (FIG. 3A) and Week 52 (FIG. 3B) is shown. Statistical analyses at Week 24 were evaluated using a non-parametric ANCOVA model, with linear extrapolation for missing data. Data to Week 52 represent those subjects randomized to secukinumab at baseline only. *P<0.05 versus placebo.

DETAILED DESCRIPTION OF THE DISCLOSURE

Figure 1:
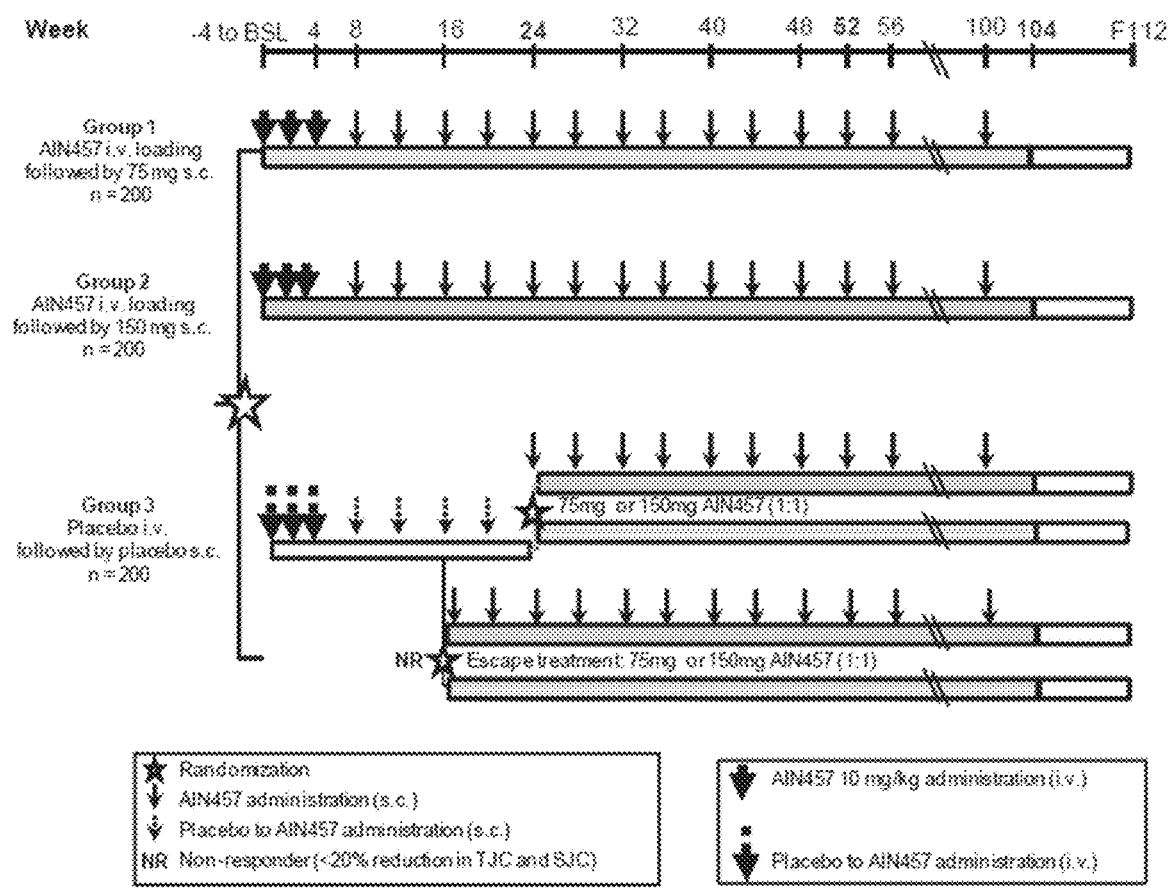
FIG. 1. AIN457F2306 study design.

It is an object of the disclosure to provide methods for inhibiting structural damage (e.g., bone and/or joint) in psoriatic arthritis (PsA) patients using IL-17 antagonists, e.g., secukinumab.

The term "comprising" encompasses "including" and "consisting," e.g., a composition "comprising" X may consist exclusively of X or may include something additional e.g. X+Y.

As used herein, the phrase "inhibiting the progression of structural damage" is synonymous with "preventing the progression of structural damage," and is used to mean reducing, abrogating or slowing the bone and/or joint damage that is associated with PsA. Such bone and/or joint damage includes, e.g., erosion, joint space narrowing (JSN), pencil-in-cup phenomena, widening, narrowing, subluxation, bony proliferation, osteolysis, and/or ankylosis. Various radiographic scoring methods exist to measure the progression of structural damage in PsA patients, e.g., modified Steinbrocker, sharp scoring, mTSS (also referred to as vdH-mTSS), and Ratingen score (see, e.g., van der Heijde (2005) Ann. Rheum. Dis. 64:ii61-ii64). In some embodiments, the mTSS (also referred to as vdH-mTSS) is used to assess progression of structural damage in a PsA patient. In some embodiments, inhibiting the progression of structural damage is defined as a change from baseline in vdH-mTSS of <0.57, ≤0.5, ≤0.3, ≤0.25, ≤0.20, ≤0.15, ≤0.13, ≤0.10, ≤0.05, or ≤0.02, and may include maintenance of this effect over time. Change from baseline can be measured at any given time point, e.g., 24 weeks after beginning of treatment, 52 weeks after beginning of treatment. In some embodiments, inhibition of structural progression is defined as a change in mTSS score of ≤0.5 from baseline.

Inhibiting the progression of structural damage may also be assessed by analyzing particular types of bond and joint damage (e.g., erosion, joint space narrowing (JSN), pencil-in-cup phenomena, widening, narrowing, subluxation, bony proliferation, osteolysis, and/or ankyloses). In some embodiments, radiographic imaging of erosion is used to assess progression of structural damage in a PsA patient. In some embodiments, inhibiting the progression of structural damage is defined as a change from baseline in erosion score of ≤0.35, ≤0.30, ≤0.25, ≤0.2, ≤0.15, ≤0.1, ≤0.08, ≤0.05, ≤0.03. In some embodiments, radiographic imaging of JSN is used to assess progression of structural damage in a PsA patient. In some embodiments, inhibiting the progression of structural damage is defined as a change from baseline in JSN score of ≤0.23, ≤0.20, ≤0.15, ≤0.10, ≤0.05, ≤or 0.02.

In addition to radiographic imaging, other methods useful to visualize changes in bone and/or joint structure include MRI and ultrasound, e.g., Power Doppler and Grayscale ultrasound (PDUS). The scoring system used to evaluate changes in bone and/or joint structure will depend on the visualization mode selected by a physician, e.g., the OMER- ACT-EULAR composite PDUS score may used to evaluate synovial activity when PDUS is applied.

The term "about" in relation to a numerical value x means, for example, +/−10%. When used in front of a numerical range or list of numbers, the term "about" applies to each number in the series, e.g., the phrase "about 1-5" should be interpreted as "about 1-about 5", or, e.g., the phrase "about 1, 2, 3, 4" should be interpreted as "about 1, about 2, about 3, about 4, etc."

The word "substantially" does not exclude "completely," e.g., a composition which is "substantially free" from Y may be completely free from Y. Where necessary, the word "substantially" may be omitted from the definition of the disclosure.

The term "antibody" as used herein refers to whole antibodies. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The $V_H$ and $V_L$ regions can be further subdivided into regions of hypervariability, termed hypervariable regions or complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding fragment" of an antibody as used herein, refers to fragments (including single chains) of an antibody that retain the ability to specifically bind to an antigen (e.g., IL-17). It has been shown that the antigen-binding function of an antibody can be performed by fragments of a full-length antibody. Examples of binding fragments encompassed within the term "antigen-binding fragment" of an antibody include a Fab fragment, a monovalent fragment consisting of the $V_L$, $V_H$, CL and CH1 domains; a F(ab)2 fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated CDR. Exemplary antigen-binding sites include the CDRs of secukinumab as set forth in SEQ ID NOs:1-6 and 11-13 (Table 1), preferably the heavy chain CDR3. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies are also intended to be encompassed within the phrase "antigen-binding fragment". Single chain antibodies and other antigen-binding fragments are obtained using conventional techniques known to those of skill in the art.

An "isolated antibody", as used herein, refers to an antibody that is substantially free of other antibodies having different antigenic specificities (e.g., an isolated antibody that specifically binds IL-17 is substantially free of antibodies that specifically bind antigens other than IL-17). The term "monoclonal antibody" or "monoclonal antibody composition" as used herein refer to a preparation of antibody molecules of single molecular composition. The term "human antibody", as used herein, is intended to include antibodies having variable regions in which both the framework and CDR regions are derived from sequences of human origin. A "human antibody" need not be produced by a human, human tissue or human cell. The human antibodies of the disclosure may include amino acid residues not encoded by human sequences (e.g., mutations introduced by random or site-specific mutagenesis in vitro, by N-nucleotide addition at junctions in vivo during recombination of antibody genes, or by somatic mutation in vivo). In some embodiments of the disclosed processes and compositions, the IL-17 antibody is a human antibody, an isolated antibody, and/or a monoclonal antibody.

The term "IL-17" refers to IL-17A, formerly known as CTLA8, and includes wild-type IL-17A from various species (e.g., human, mouse, and monkey), polymorphic variants of IL-17A, and functional equivalents of IL-17A. Functional equivalents of IL-17A according to the present disclosure preferably have at least about 65%, 75%, 85%, 95%, 96%, 97%, 98%, or even 99% overall sequence identity with a wild-type IL-17A (e.g., human IL-17A), and substantially retain the ability to induce IL-6 production by human dermal fibroblasts.

The term "$K_D$" is intended to refer to the dissociation rate of a particular antibody-antigen interaction. The term "$K_D$", as used herein, is intended to refer to the dissociation constant, which is obtained from the ratio of $K_D$ to $K_a$ (i.e. $K_d/K_a$) and is expressed as a molar concentration (M). $K_D$ values for antibodies can be determined, e.g., by using surface plasmon resonance, or a biosensor system (e.g., Biacore®). In some embodiments, the IL-17 antibody or antigen-binding fragment thereof, e.g., secukinumab, binds human IL-17 with a $K_D$ of ~100-250 pM.

The term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. Standard assays to evaluate the binding affinity of the antibodies toward IL-17 of various species are known in the art, including for example, ELISAs, western blots and RIAs. The binding kinetics (e.g., binding affinity) of the antibodies also can be assessed by standard assays known in the art, such as by Biacore®analysis.

An antibody that "inhibits" one or more of these IL-17 functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (or when a control antibody of irrelevant specificity is present). An antibody that inhibits IL-17 activity affects a statistically significant decrease, e.g., by at least about 10% of the measured parameter, by at least 50%, 80% or 90%, and in certain embodiments of the disclosed methods and compositions, the IL-17 antibody used may inhibit greater than 95%, 98% or 99% of IL-17 functional activity.

"Inhibit IL-6" as used herein refers to the ability of an IL-17 antibody or antigen-binding fragment thereof (e.g., secukinumab) to decrease IL-6 production from primary human dermal fibroblasts. The production of IL-6 in primary human (dermal) fibroblasts is dependent on IL-17 (Hwang et al., (2004) Arthritis Res Ther; 6:R120-128). In short, human dermal fibroblasts are stimulated with recombinant IL-17 in the presence of various concentrations of an IL-17 binding molecule or human IL-17 receptor with Fc part. The chimeric anti-CD25 antibody Simulect® (basiliximab) may be conveniently used as a negative control. Supernatant is taken after 16 h stimulation and assayed for IL-6 by ELISA. An IL-17 antibody or antigen-binding fragment thereof, e.g., secukinumab, typically has an $IC_{50}$ for inhibition of IL-6 production (in the presence 1 nM human IL-17) of about 50 nM or less (e.g., from about 0.01 to about 50 nM) when tested as above, i.e., said inhibitory activity being measured on IL-6 production induced by hu-IL-17 in human dermal fibroblasts. In some embodiments of the disclosed methods uses and kits, IL-17 antibodies or antigen-binding fragments thereof, e.g., secukinumab, and functional derivatives thereof have an $IC_{50}$ for inhibition of IL-6 production as defined above of about 20 nM or less, more preferably of about 10 nM or less, more preferably of about 5 nM or less, more preferably of about 2 nM or less, more preferably of about 1 nM or less.

The term "derivative", unless otherwise indicated, is used to define amino acid sequence variants, and covalent modifications (e.g., pegylation, deamidation, hydroxylation, phosphorylation, methylation, etc.) of an IL-17 antibody or antigen-binding fragment thereof, e.g., secukinumab, according to the present disclosure, e.g., of a specified sequence (e.g., a variable domain). A "functional derivative" includes a molecule having a qualitative biological activity in common with the disclosed IL-17 antibodies. A functional derivative includes fragments and peptide analogs of an IL-17 antibody as disclosed herein. Fragments comprise regions within the sequence of a polypeptide according to the present disclosure, e.g., of a specified sequence. Functional derivatives of IL-17 antibodies disclosed herein (e.g., functional derivatives of secukinumab) preferably comprise $V_H$ and/or $V_L$ domains that have at least about 65%, 75%, 85%, 95%, 96%, 97%, 98%, or even 99% overall sequence identity with the $V_H$ and/or $V_L$ sequences of the IL-17 antibodies and antigen-binding fragments thereof disclosed herein (e.g., the $V_H$ and/or $V_L$ sequences of Table 1), and substantially retain the ability to bind human IL-17 or, e.g., inhibit IL-6 production of IL-17 induced human dermal fibroblasts.

The phrase "substantially identical" means that the relevant amino acid or nucleotide sequence (e.g., $V_H$ or $V_L$ domain) will be identical to or have insubstantial differences (e.g., through conserved amino acid substitutions) in comparison to a particular reference sequence. Insubstantial differences include minor amino acid changes, such as 1 or 2 substitutions in a 5 amino acid sequence of a specified region (e.g., $V_H$ or $V_L$ domain). In the case of antibodies, the second antibody has the same specificity and has at least 50% of the affinity of the same. Sequences substantially identical (e.g., at least about 85% sequence identity) to the sequences disclosed herein are also part of this application. In some embodiments, the sequence identity of a derivative IL-17 antibody (e.g., a derivative of secukinumab, e.g., a secukinumab biosimilar antibody) can be about 90% or greater, e.g., 90%, 91%, 92%, 93%, 94%, 95%, 96%, 97%, 98%, 99% or higher relative to the disclosed sequences.

"Identity" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent identity, and not considering any conservative substitutions as part of the sequence identity. Neither N- or C-terminal extensions nor insertions shall be construed as reducing identity. Methods and computer programs for the alignment are well known. The percent identity can be determined by standard alignment algorithms, for example, the Basic Local Alignment Search Tool (BLAST) described by Altshul et al. ((1990) J. Mol. Biol., 215: 403410); the algorithm of Needleman et al. ((1970) J. Mol. Biol., 48: 444453); or the algorithm of Meyers et al. ((1988) Comput. Appl. Biosci., 4: 1117). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

"Amino acid(s)" refer to all naturally occurring L-a-amino acids, e.g., and include D-amino acids. The phrase "amino acid sequence variant" refers to molecules with some differences in their amino acid sequences as compared to the sequences according to the present disclosure. Amino acid sequence variants of an antibody according to the present disclosure, e.g., of a specified sequence, still have the ability to bind the human IL-17 or, e.g., inhibit IL-6 production of IL-17 induced human dermal fibroblasts. Amino acid sequence variants include substitutional variants (those that have at least one amino acid residue removed and a different amino acid inserted in its place at the same position in a polypeptide according to the present disclosure), insertional variants (those with one or more amino acids inserted immediately adjacent to an amino acid at a particular position in a polypeptide according to the present disclosure) and deletional variants (those with one or more amino acids removed in a polypeptide according to the present disclosure).

As used herein, "monthly" is used to mean 30 days or 4 weeks, as the context may dictate.

As used herein, the phrase "biologic-naïve" refers to a PsA patient who has not been previously treated with a biological agent, e.g., ustekinumab, a TNF alpha inhibitor, etc. As used herein, the phrase "biologic-experienced" refers to a PsA patient who has been previously treated with a biological agent for PsA, e.g., ustekinumab, a TNF alpha inhibitor, etc. As used herein, the phrases "has not previously been treated with a TNF antagonist" and "TNF naïve" refer to a PsA patient who has not been previously treated with a TNF alpha inhibitor for PsA. As used herein, the phrases "has previously been treated with a TNF antagonist" and "TNF experienced" refer to a PsA patient who has been previously treated with a TNF alpha inhibitor (e.g., infliximab, etanercept, adalimumab, certolizumab, golimumab). It includes patients who were refractory to or had an inadequate response to TNF alpha inhibitor treatment, as well as patients who stopped treatment with the TNF alpha inhibitor for safety or tolerability reasons. As used herein, the phrases "had an inadequate response to previous treatment with the TNF antagonist," "TNF-inadequate responder" and "TNF-IR" refer to a PsA patient who has been previously treated with a TNF alpha inhibitor for PsA (e.g., infliximab, etanercept, adalimumab, certolizumab, golimumab), but whose symptoms (e.g., skin and/or joint symptoms) were not adequately controlled by the TNF alpha inhibitor (e.g., a patient with active PsA despite at least 4 weeks, at least 8 weeks, at least 3 months, at least 14 weeks, or at least 4 months of treatment using an approved dose of the anti-TNF agent). In some embodiments of the disclosed methods, kits, IL-17 antagonists and uses, the patient is biologic-naïve, biologic-experienced, TNF naïve, TNF experienced, or TNF-IR.

As used herein, "selecting" and "selected" in reference to a patient is used to mean that a particular patient is specifically chosen from a larger group of patients on the basis of (due to) the particular patient having a predetermined criteria. Similarly, "selectively treating" refers to providing treatment to a patient having a particular disease, where that patient is specifically chosen from a larger group of patients on the basis of the particular patient having a predetermined criteria. Similarly, "selectively administering" refers to administering a drug to a patient that is specifically chosen from a larger group of patients on the basis of (due to) the particular patient having a predetermined criteria. By selecting, selectively treating and selectively administering, it is meant that a patient is delivered a personalized therapy based on the patient's personal history (e.g., prior therapeutic interventions, e.g., prior treatment with biologicals, e.g., prior treatment with a TNF alpha antagonist) and/or biology, rather than being delivered a standard treatment regimen based solely on the patient having a particular disease. Selecting, in reference to a method of treatment as used herein, does not refer to fortuitous treatment of a patient having a particular criteria, but rather refers to the deliberate choice to administer treatment to a patient based on the patient having a particular criteria. Thus, selective treatment/administration differs from standard treatment/administration, which delivers a particular drug to all patients with a given disease, regardless of their history and/or biology.

As used herein, "selecting a patient for treatment on the basis of the patient having previously been treated with a TNF antagonist" and the like is used to mean that a particular PsA patient is chosen from a larger group or PsA patients based on that particular patient's prior exposure to a TNF alpha antagonist. In some embodiments of the disclosed methods, kits, IL-17 antagonists and uses, a PsA patient is selected treatment with an IL-17 antagonist (e.g., secukinumab) based on the patient having previously been administered a TNF alpha antagonist.

As used herein, "DMARD" refers to a disease-modifying antirheumatic drug, e.g., methotrexate.

As used herein, "active PsA" refers to active psoriatic arthritis, defined as >3 swollen and >3 tender joints. In some embodiments, the patient to be treated has active PsA.

As used herein, a patient having "concomitant psoriasis" refers to PsA patient who additionally has plaque-type psoriasis. In some embodiments of the disclosed methods, kits, IL-17 antagonists and uses, the patient has concomitant psoriasis, e.g., concomitant moderate to severe plaque-type psoriasis. Clinicians usually define moderate-to-severe psoriasis as patients having a body surface area (BSA) of >10 or a psoriasis area and severity index of (PASI) of >10, coupled with a dermatology life quality index (DLQI) of >10 (see, e.g., Mrowietz et al. (2011) Arch. Dermatol. Res. 303:1-10).

IL-17 Antagonists

The various disclosed processes, kits and methods utilize an IL-17 antagonist, e.g., IL-17 binding molecule (e.g., soluble IL-17 receptor, IL-17 antibody or antigen-binding fragment thereof, e.g., secukinumab) or IL-17 receptor binding molecule (e.g., IL-17 receptor antibody or antigen-binding fragment thereof). In some embodiments, the IL-17 antagonist is an IL-17 binding molecule, preferably an IL-7 antibody or antigen-binding fragment thereof.

In one embodiment, the IL-17 antibody or antigen-binding fragment thereof comprises at least one immunoglobulin heavy chain variable domain ($V_H$) comprising hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3. In one embodiment, the IL-17 antibody or antigen-binding fragment thereof comprises at least one immunoglobulin light chain variable domain ($V_L$') comprising hypervariable regions CDR1', CDR2' and CDR3', said CDR1' having the amino acid sequence SEQ ID NO:4, said CDR2' having the amino acid sequence SEQ ID NO:5 and said CDR3' having the amino acid sequence SEQ ID NO:6. In one embodiment, the IL-17 antibody or antigen-binding fragment thereof comprises at least one immunoglobulin heavy chain variable domain ($V_H$) comprising hypervariable regions CDR1-x, CDR2-x and CDR3-x, said CDR1-x having the amino acid sequence SEQ ID NO:11, said CDR2-x having the amino acid sequence SEQ ID NO:12, and said CDR3-x having the amino acid sequence SEQ ID NO:13.

In one embodiment, the IL-17 antibody or antigen-binding fragment thereof comprises at least one immunoglobulin (Ig) $V_H$ domain and at least one immunoglobulin $V_L$ domain, wherein: a) the Ig $V_H$ domain comprises (e.g., in sequence): i) hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; or ii) hypervariable regions CDR1-x, CDR2-x and CDR3-x, said CDR1-x having the amino acid sequence SEQ ID NO:11, said CDR2-x having the amino acid sequence SEQ ID NO:12, and said CDR3-x having the amino acid sequence SEQ ID NO:13; and b) the Ig $V_L$ domain comprises (e.g., in sequence) hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6.

In one embodiment, the IL-17 antibody or antigen-binding fragment thereof comprises: a) an immunoglobulin heavy chain variable domain ($V_H$) comprising the amino acid sequence set forth as SEQ ID NO:8; b) an Ig light chain variable domain ($V_L$) comprising the amino acid sequence set forth as SEQ ID NO:10; c) an Ig $V_H$ domain comprising the amino acid sequence set forth as SEQ ID NO:8 and an Ig $V_L$ domain comprising the amino acid sequence set forth as SEQ ID NO:10; d) an Ig $V_H$ domain comprising the hypervariable regions set forth as SEQ ID NO:1, SEQ ID NO:2, and SEQ ID NO:3; e) an Ig $V_L$ domain comprising the hypervariable regions set forth as SEQ ID NO:4, SEQ ID NO:5 and SEQ ID NO:6; f) an Ig $V_H$ domain comprising the hypervariable regions set forth as SEQ ID NO:11, SEQ ID NO:12 and SEQ ID NO:13; g) an Ig $V_H$ domain comprising the hypervariable regions set forth as SEQ ID NO:1, SEQ ID NO:2, and SEQ ID NO:3 and an Ig $V_L$ domain comprising the hypervariable regions set forth as SEQ ID NO:4, SEQ ID NO:5 and SEQ ID NO:6; or h) an Ig $V_H$ domain comprising the hypervariable regions set forth as SEQ ID NO:11, SEQ ID NO:12 and SEQ ID NO:13 and an Ig V$_L$ domain comprising the hypervariable regions set forth as SEQ ID NO:4, SEQ ID NO:5 and SEQ ID NO:6.

For ease of reference, the amino acid sequences of the hypervariable regions of the secukinumab monoclonal antibody, based on the Kabat definition and as determined by the X-ray analysis and using the approach of Chothia and coworkers, is provided in Table 1, below.

secukinumab antibody. It consists in sequence, e.g. of FR1 (amino acid 1 to 30 of SEQ ID NO:8), FR2 (amino acid 36 to 49 of SEQ ID NO:8), FR3 (amino acid 67 to 98 of SEQ ID NO:8) and FR4 (amino acid 117 to 127 of SEQ ID NO:8) regions. Taking into consideration the determined hypervariable regions of secukinumab by X-ray analysis, another preferred heavy chain framework consists in sequence of FR1-x (amino acid 1 to 25 of SEQ ID NO:8), FR2-x (amino

TABLE 1

Amino acid sequences of the hypervariable regions of the secukinumab monoclonal antibodies.

Light-Chain

| | | |
|---|---|---|
| CDR1' | Kabat | R-A-S-Q-S-V-S-S-S-Y-L-A (SEQ ID NO: 4) |
| | Chothia | R-A-S-Q-S-V-S-S-S-Y-L-A (SEQ ID NO: 4) |
| CDR2' | Kabat | G-A-S-S-R-A-T (SEQ ID NO: 5) |
| | Chothia | G-A-S-S-R-A-T (SEQ ID NO: 5) |
| CDR2' | Kabat | Q-Q-Y-G-S-S-P-C-T (SEQ ID NO: 6) |
| | Chothia | Q-Q-Y-G-S-S-P-C-T (SEQ ID NO: 6) |

Heavy-Chain

| | | |
|---|---|---|
| CDR1 | Kabat | N-Y-W-M-N (SEQ ID NO: 1) |
| CDR1-x | Chothia | G-F-T-F-S-N-Y-W-M-N (SEQ ID NO: 11) |
| CDR2 | Kabat | A-I-N-Q-D-G-S-E-K-Y-Y-V-G-S-V-K-G (SEQ ID NO: 2) |
| CDR2-x | Chothia | A-I-N-Q-D-G-S-E-K-Y-Y (SEQ ID NO: 12) |
| CDR3 | Kabat | D-Y-Y-D-I-L-T-D-Y-Y-I-H-Y-W-Y-F-D-L (SEQ ID NO: 3) |
| CDR3-x | Chothia | C-V-R-D-Y-Y-D-I-L-T-D-Y-Y-I-H-Y-W-Y-F-D-L-W-G (SEQ ID NO: 13) |

In preferred embodiments, the constant region domains preferably also comprise suitable human constant region domains, for instance as described in "Sequences of Proteins of Immunological Interest", Kabat E. A. et al, US Department of Health and Human Services, Public Health Service, National Institute of Health. DNA encoding the VL of secukinumab is set forth in SEQ ID NO:9. DNA encoding the V$_H$ of secukinumab is set forth in SEQ ID NO:7.

In some embodiments, the IL-17 antibody or antigen-binding fragment thereof (e.g., secukinumab) comprises the three CDRs of SEQ ID NO:10. In other embodiments, the IL-17 antibody or antigen-binding fragment thereof comprises the three CDRs of SEQ ID NO:8. In other embodiments, the IL-17 antibody or antigen-binding fragment thereof comprises the three CDRs of SEQ ID NO:10 and the three CDRs of SEQ ID NO:8. CDRs of SEQ ID NO:8 and SEQ ID NO:10 may be found in Table 1.

In some embodiments, IL-17 antibody or antigen-binding fragment thereof comprises the light chain of SEQ ID NO:14. In other embodiments, the IL-17 antibody or antigen-binding fragment thereof comprises the heavy chain of SEQ ID NO:15. In other embodiments, the IL-17 antibody or antigen-binding fragment thereof comprises the light chain of SEQ ID NO:14 and the heavy domain of SEQ ID NO:15. In some embodiments, the IL-17 antibody or antigen-binding fragment thereof comprises the three CDRs of SEQ ID NO:14. In other embodiments, IL-17 antibody or antigen-binding fragment thereof comprises the three CDRs of SEQ ID NO:15. In other embodiments, the IL-17 antibody or antigen-binding fragment thereof comprises the three CDRs of SEQ ID NO:14 and the three CDRs of SEQ ID NO:15. CDRs of SEQ ID NO:14 and SEQ ID NO:15 may be found in Table 1.

Hypervariable regions may be associated with any kind of framework regions, though preferably are of human origin. Suitable framework regions are described in Kabat E. A. et al, ibid. The preferred heavy chain framework is a human heavy chain framework, for instance that of the secukinumab antibody. It consists in sequence, e.g. of FR1 acid 36 to 49 of SEQ ID NO:8), FR3-x (amino acid 61 to 95 of SEQ ID NO:8) and FR4 (amino acid 119 to 127 of SEQ ID NO:8) regions. In a similar manner, the light chain framework consists, in sequence, of FR1' (amino acid 1 to 23 of SEQ ID NO:10), FR2' (amino acid 36 to 50 of SEQ ID NO:10), FR3' (amino acid 58 to 89 of SEQ ID NO:10) and FR4' (amino acid 99 to 109 of SEQ ID NO:10) regions.

In one embodiment, the IL-17 antibody or antigen-binding fragment thereof, e.g., secukinumab, is a human IL-17 antibody that comprises at least: a) an immunoglobulin heavy chain or fragment thereof which comprises a variable domain comprising, in sequence, the hypervariable regions CDR1, CDR2 and CDR3 and the constant part or fragment thereof of a human heavy chain; said CDR1 having the amino acid sequence SEQ ID NO:1, said CDR2 having the amino acid sequence SEQ ID NO:2, and said CDR3 having the amino acid sequence SEQ ID NO:3; or b) an immunoglobulin light chain or fragment thereof which comprises a variable domain comprising, in sequence, the hypervariable regions CDR1', CDR2', and CDR3' and the constant part or fragment thereof of a human light chain, said CDR1' having the amino acid sequence SEQ ID NO: 4, said CDR2' having the amino acid sequence SEQ ID NO:5, and said CDR3' having the amino acid sequence SEQ ID NO:6.

In one embodiment, the IL-17 antibody or antigen-binding fragment thereof is selected from a single chain antibody or antigen-binding fragment thereof that comprises an antigen-binding site comprising: a) a first domain comprising, in sequence, the hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; and b) a second domain comprising, in sequence, the hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6; and c) a peptide linker which is bound either to the N-terminal extremity of the first domain and to the C-terminal extremity of the second domain or to the C-terminal extremity of the first domain and to the N-terminal extremity of the second domain.

Alternatively, an IL-17 antibody or antigen-binding fragment thereof as used in the disclosed methods may comprise a derivative of the IL-17 antibodies set forth herein by sequence (e.g., a pegylated version of secukinumab). Alternatively, the $V_H$ or $V_L$ domain of an IL-17 antibody or antigen-binding fragment thereof used in the disclosed methods may have $V_H$ or $V_L$ domains that are substantially identical to the $V_H$ or $V_L$ domains set forth herein (e.g., those set forth in SEQ ID NO:8 and 10). A human IL-17 antibody disclosed herein may comprise a heavy chain that is substantially identical to that set forth as SEQ ID NO:15 and/or a light chain that is substantially identical to that set forth as SEQ ID NO:14. A human IL-17 antibody disclosed herein may comprise a heavy chain that comprises SEQ ID NO:15 and a light chain that comprises SEQ ID NO:14. A human IL-17 antibody disclosed herein may comprise: a) one heavy chain, comprising a variable domain having an amino acid sequence substantially identical to that shown in SEQ ID NO:8 and the constant part of a human heavy chain; and b) one light chain, comprising a variable domain having an amino acid sequence substantially identical to that shown in SEQ ID NO:10 and the constant part of a human light chain.

Alternatively, an IL-17 antibody or antigen-binding fragment thereof used in the disclosed methods may be an amino acid sequence variant of the reference IL-17 antibodies set forth herein. The disclosure also includes IL-17 antibodies or antigen-binding fragments thereof (e.g., secukinumab) in which one or more of the amino acid residues of the $V_H$ or $V_L$ domain of secukinumab (e.g., Cys97 of the light chain), typically only a few (e.g., 1-10), are changed; for instance by mutation, e.g., site directed mutagenesis of the corresponding DNA sequences. In all such cases of derivative and variants, the IL-17 antibody or antigen-binding fragment thereof is capable of inhibiting the activity of about 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50%, said inhibitory activity being measured on IL-6 production induced by hu-IL-17 in human dermal fibroblasts as described in Example 1 of WO 2006/013107.

In some embodiments, the IL-17 antibodies or antigen-binding fragments thereof, e.g., secukinumab, bind to an epitope of mature human IL-17 comprising Leu74, Tyr85, His86, Met87, Asn88, Val124, Thr125, Pro126, Ile127, Val128, His129. In some embodiments, the IL-17 antibody, e.g., secukinumab, binds to an epitope of mature human IL-17 comprising Tyr43, Tyr44, Arg46, Ala79, Asp80. In some embodiments, the IL-17 antibody, e.g., secukinumab, binds to an epitope of an IL-17 homodimer having two mature human IL-17 chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain. The residue numbering scheme used to define these epitopes is based on residue one being the first amino acid of the mature protein (i.e., IL-17A lacking the 23 amino acid N-terminal signal peptide and beginning with Glycine). The sequence for immature IL-17A is set forth in the Swiss-Prot entry Q16552. In some embodiments, the IL-17 antibody has a $K_D$ of about 100-200 pM. In some embodiments, the IL-17 antibody has an $IC_{50}$ of about 0.4 nM for in vitro neutralization of the biological activity of about 0.67 nM human IL-17A. In some embodiments, the absolute bioavailability of subcutaneously (s.c.) administered IL-17 antibody has a range of about 60-about 80%, e.g., about 76%. In some embodiments, the IL-17 antibody, such as secukinumab, has an elimination half-life of about 4 weeks (e.g., about 23 to about 35 days, about 23 to about 30 days, e.g., about 30 days). In some embodiments, the IL-17 antibody (such as secukinumab) has a $T_{max}$ of about 7-8 days.

Particularly preferred IL-17 antibodies or antigen-binding fragments thereof used in the disclosed methods are human antibodies, especially secukinumab as described in Examples 1 and 2 of WO 2006/013107. Secukinumab is a recombinant high-affinity, fully human monoclonal anti-human interleukin-17A (IL-17A, IL-17) antibody of the IgG1/kappa isotype that is currently in clinical trials for the treatment of immune-mediated inflammatory conditions. Secukinumab (see, e.g., WO2006/013107 and WO2007/117749) has a very high affinity for IL-17, i.e., a $K_D$ of about 100-200 pM and an $IC_{50}$ for in vitro neutralization of the biological activity of about 0.67 nM human IL-17A of about 0.4 nM. Thus, secukinumab inhibits antigen at a molar ratio of about 1:1. This high binding affinity makes the secukinumab antibody particularly suitable for therapeutic applications. Furthermore, it has been determined that secukinumab has a very long half-life (~4 weeks), which allows for prolonged periods between administration, an exceptional property when treating chronic life-long disorders, such as PsA.

Other preferred IL-17 antagonists for use in the disclosed methods, kits and regimens are broadalumab and other antagonists set forth in U.S. Pat. No. 7,767,206 (WO08054603) and the IL-17 antibodies set forth in U.S. Pat. Nos: 8,057,794; 8,003,099; 8,110,191; and 7,838,638 and US Published Patent Application Nos: 20120034656 and 20110027290, which are incorporated by reference herein in their entirety.

Methods of Treatment and Uses of IL-17 Antagonists

The disclosed IL-17 antagonists, e.g., IL-17 binding molecules (e.g., IL-17 antibody or antigen-binding fragment thereof, e.g., secukinumab) or IL-17 receptor binding molecules (e.g., IL-17 antibody or antigen-binding fragment thereof), may be used in vitro, ex vivo, or incorporated into pharmaceutical compositions and administered to individuals (e.g., human patients) in vivo to inhibit the progression of structural damage in PsA patients, e.g., in PsA patients that have not previously been treated with a TNF inhibitor (TNF-naïve patients) and PsA patients that have been previously treated with a TNF inhibitor, e.g., patients having been treated with a TNF inhibitor, but who had an inadequate response (e.g., failed or less than desirable) thereto (TNF-IR patients).

The IL-17 antagonists, e.g., IL-17 binding molecules (e.g., IL-17 antibody or antigen-binding fragment thereof, e.g., secukinumab) or IL-17 receptor binding molecules (e.g., IL-17 receptor antibody or antigen-binding fragment thereof), may be used as a pharmaceutical composition when combined with a pharmaceutically acceptable carrier. Such a composition may contain, in addition to an IL-17 antagonist, carriers, various diluents, fillers, salts, buffers, stabilizers, solubilizers, and other materials well known in the art. The characteristics of the carrier will depend on the route of administration. The pharmaceutical compositions for use in the disclosed methods may also contain additional therapeutic agents for treatment of the particular targeted disorder. For example, a pharmaceutical composition may also include anti-inflammatory agents. Such additional factors and/or agents may be included in the pharmaceutical composition to produce a synergistic effect with the IL-17 binding molecules, or to minimize side effects caused by the IL-17 antagonists, e.g., IL-17 binding molecules (e.g., IL-17 antibody or antigen-binding fragment thereof, e.g., secukinumab) or IL-17 receptor binding molecules (e.g., IL-17 receptor antibody or antigen-binding fragment thereof).

Pharmaceutical compositions for use in the disclosed methods may be manufactured in conventional manner. In one embodiment, the pharmaceutical composition is provided in lyophilized form. For immediate administration it is dissolved in a suitable aqueous carrier, for example sterile water for injection or sterile buffered physiological saline. If it is considered desirable to make up a solution of larger volume for administration by infusion rather than a bolus injection, may be advantageous to incorporate human serum albumin or the patient's own heparinized blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution. Other formulations comprise liquid or lyophilized formulation.

Antibodies, e.g., antibodies to IL-17, are typically formulated either in aqueous form ready for parenteral administration or as lyophilisates for reconstitution with a suitable diluent prior to administration. In some embodiments of the disclosed methods and uses, the IL-17 antagonist, e.g., IL-17 antibody, e.g., secukinumab, is formulated as a lyophilisate. Suitable lyophilisate formulations can be reconstituted in a small liquid volume (e.g., 1 ml) to allow subcutaneous administration and can provide solutions with low levels of antibody aggregation. The use of antibodies as the active ingredient of pharmaceuticals is now widespread, including the products HERCEPTIN™ (trastuzumab), RITUXAN™ (rituximab), SYNAGIS™ (palivizumab), etc. Techniques for purification of antibodies to a pharmaceutical grade are well known in the art. When a therapeutically effective amount of an IL-17 antagonist, e.g., IL-17 binding molecules (e.g., IL-17 antibody or antigen-binding fragment thereof, e.g., secukinumab) or IL-17 receptor binding molecules (e.g., IL-17 receptor antibody or antigen-binding fragment thereof) is administered by intravenous, cutaneous or subcutaneous injection, the IL-17 antagonist will be in the form of a pyrogen-free, parenterally acceptable solution. A pharmaceutical composition for intravenous, cutaneous, or subcutaneous injection may contain, in addition to the IL-17 antagonist, an isotonic vehicle such as sodium chloride, Ringer's, dextrose, dextrose and sodium chloride, lactated Ringer's, or other vehicle as known in the art.

The appropriate dosage will vary depending upon, for example, the particular IL-17 antagonists, e.g., IL-17 binding molecules (e.g., IL-17 antibody or antigen-binding fragment thereof, e.g., secukinumab) or IL-17 receptor binding molecules (e.g., IL-17 receptor antibody or antigen-binding fragment thereof) to be employed, the host, the mode of administration and the nature and severity of the condition being treated, and on the nature of prior treatments that the patient has undergone. Ultimately, the attending health care provider will decide the amount of the IL-17 antagonist with which to treat each individual patient. In some embodiments, the attending health care provider may administer low doses of the IL-17 antagonist and observe the patient's response. In other embodiments, the initial dose(s) of IL-17 antagonist administered to a patient are high, and then are titrated downward until signs of relapse occur. Larger doses of the IL-17 antagonist may be administered until the optimal therapeutic effect is obtained for the patient, and the dosage is not generally increased further.

In practicing some of the methods of treatment or uses of the present disclosure, a therapeutically effective amount of an IL-17 antagonist, e.g., IL-17 binding molecule (e.g., IL-17 antibody or antigen-binding fragment thereof, e.g., secukinumab) or IL-17 receptor binding molecule (e.g., IL-17 receptor antibody or antigen-binding fragment thereof) is administered to a patient, e.g., a mammal (e.g., a human). While it is understood that the disclosed methods provide for treatment of PsA patients using an IL-17 antagonist (e.g., secukinumab), this does not preclude that, if the patient is to be ultimately treated with an IL-17 antagonist, such IL-17 antagonist therapy is necessarily a monotherapy. Indeed, if a patient is selected for treatment with an IL-17 antagonist, then the IL-17 antagonist (e.g., secukinumab) may be administered in accordance with the methods of the disclosure either alone or in combination with other agents and therapies for treating PsA patients, e.g., in combination with at least one additional PsA agent, such as an immunosuppressive agent, a disease-modifying anti-rheumatic drug (DMARD) (e.g., MTX), a pain-control drug (e.g., tramadol or paracetamol), a steroid (e.g., prednisone), a non-steroidal anti-inflammatory drug (NSAID), a cytokine antagonist, a bone anabolic, a bone anti-resorptive, and combinations thereof (e.g., dual and triple therapies). When coadministered with one or more additional agents, an IL-17 antagonist may be administered either simultaneously with the other agent, or sequentially. If administered sequentially, the attending physician will decide on the appropriate sequence of administering the IL-17 antagonist in combination with other agents, as well as the appropriate dosages for co-delivery.

Non-steroidal anti-inflammatory drugs and pain control agents useful in combination with secukinumab for the treatment of PsA patients include, propionic acid derivative, acetic acid derivative, enolic acid derivatives, fenamic acid derivatives, Cox inhibitors, e.g., lumiracoxib, ibuprophen, fenoprofen, ketoprofen, flurbiprofen, oxaprozin, indomethacin, sulindac, etodolac, ketorolac, nabumetone, aspirin, naproxen, valdecoxib, etoricoxib, MK0966; rofecoxib, acetominophen, Celecoxib, Diclofenac, tramadol, piroxicam, meloxicam, tenoxicam, droxicam, lornoxicam, isoxicam, mefanamic acid, meclofenamic acid, flufenamic acid, tolfenamic, valdecoxib, parecoxib, etodolac, indomethacin, aspirin, ibuprophen, firocoxib. DMARDs useful in combination with an IL-17 antagonist, e.g., secukinumab, for the treatment of PsA patients include, methotrexate (MTX), antimalarial drugs (e.g., hydroxychloroquine and chloroquine), sulfasalazine, Leflunomide, azathioprine, cyclosporin, gold salts, minocycline, cyclophosphamide, D-penicillamine, minocycline, auranofin, tacrolimus, myocrisin, chlorambucil. Steroids (e.g., glucocorticoids) useful in combination with an IL-17 antagonist, e.g., secukinumab, for the treatment of a PsA patient include, prednisolone, prednisone, dexamethasone, cortisol, cortisone, hydrocortisone, methylprednisolone, betamethasone, triamcinolone, beclometasome, fludrocortisone, deoxycorticosterone, aldosterone.

Biologic agents useful in combination with an IL-17 antagonist, e.g., secukinumab, for the treatment of a PsA patient include, ADALIMUMAB (Humira®), ETANERCEPT (Enbrel®), INFLIXIMAB (Remicade®; TA-650), CERTOLIZUMAB PEGOL (Cimzia®; CDP870), GOLIMUMAB (Simponi®; CNTO148), ANAKINAS (Kineret®), RITUXIMAB (Rituxan®; MabThera®), ABATACEPT (Orencia®), TOCILIZUMAB (RoActemAS/Actemra®), integrin antagonists (TYSABRI® (natalizumab)), IL-1 antagonists (ACZ885 (Ilaris), AnakinAS (Kineret®)), CD4 antagonists, further IL-17 antagonists (LY2439821, RG4934, AMG827, SCH900117, R05310074, MEDI-571, CAT-2200), IL-23 antagonists, IL-20 antagonists, IL-6 antagonists, TNF alpha antagonists (e.g., TNF alpha antagonists or TNF alpha receptor antagonsits, e.g., pegsunercept, etc.), BLyS antagonists (e.g., Atacicept, Benlysta®/LymphoStat-B® (belimumab)), P38 Inhibitors, CD20 antagonists (Ocrelizumab, Ofatumumab (Arzerra®)), Interferon gamma antagonists (Fontolizumab).

An IL-17 antagonist, e.g., secukinumab, is conveniently administered parenterally, intravenously, e.g., into the antecubital or other peripheral vein, intramuscularly, or subcutaneously. The duration of intravenous (i.v.) therapy using a pharmaceutical composition of the present disclosure will vary, depending on the severity of the disease being treated and the condition and personal response of each individual patient. Also contemplated is subcutaneous (s.c.) therapy using a pharmaceutical composition of the present disclosure. The health care provider will decide on the appropriate duration of i.v. or s.c. therapy and the timing of administration of the therapy, using the pharmaceutical composition of the present disclosure. Preferred dosing and treatment regimens (including both induction and maintenance regimens) for treating PsA patients are provided in PCT Application No. PCT/US2011/064307, which is incorporated by reference herein as it relates to doses and regimens.

In one embodiment, the IL-17 antagonist (e.g., secukinumab) is administered to the patient intravenously (i.v.) at about 10 mg/kg every other week during week 0, 2, and 4 and thereafter is administered to the patient subcutaneously (s.c.) at about 75 mg-about 300 mg (e.g., about 75 mg, about 150 mg, about 300 mg) monthly, beginning during week 8. In this manner, the patient is dosed i.v. with about 10 mg/kg during week 0, 2, 4, and then the patient is dosed s.c. with about 75 mg-about 300 mg (e.g., about 75 mg, about 150 mg, about 300 mg) of the IL-17 antagonist (e.g., secukinumab) during week 8, 12, 16, 20, etc.

In another embodiment, the IL-17 antagonist (e.g., secukinumab) is administered to the patient s.c. at about 75 mg-about 300 mg (e.g., about 75 mg, about 150 mg, about 300 mg) weekly during weeks 0, 1, 2, and 3, and thereafter is administered to the patient s.c. at about 75 mg-about 300 mg (e.g., about 75 mg, about 150 mg, about 300 mg) monthly (every 4 weeks), beginning during week 4. In this manner, the patient is dosed s.c. with about 75 mg-about 300 mg (e.g., about 75 mg, about 150 mg, about 300 mg) of the IL-17 antagonist (e.g., secukinumab) during weeks 0, 1, 2, 3, 4, 8, 12, 16, 20, etc.

Alternatively, the IL-17 antagonist, e.g., IL-17 binding molecule (e.g., IL-17 antibody or antigen-binding fragment thereof, e.g., secukinumab) or IL-17 receptor binding molecule (e.g., IL-17 receptor antibody or antigen-binding fragment thereof) may be administered to the patient without a loading regimen, e.g., secukinumab may be administered to the patient s.c. at about 75 mg-about 300 mg (e.g., about 75 mg, about 150 mg, about 300 mg) every 4 weeks (monthly). In this manner, the patient is dosed s.c. with about 75 mg-about 300 mg (e.g., about 75 mg, about 150 mg, about 300 mg) of the IL-17 antagonist (e.g., secukinumab) during weeks 0, 4, 8, 12, 16, 20, etc.

It will be understood that dose escalation may be required (e.g., during an induction and/or maintenance phase) for certain patients, e.g., patients that display inadequate response to treatment with the IL-17 antagonists, e.g., IL-17 binding molecules (e.g., IL-17 antibody or antigen-binding fragment thereof, e.g., secukinumab) or IL-17 receptor binding molecules (e.g., IL-17 receptor antibody or antigen-binding fragment thereof). Thus, s.c. dosages of secukinumab may be greater than about 75 mg to about 300 mg s.c., e.g., about 80 mg, about 100 mg, about 125 mg, about 175 mg, about 200 mg, about 250 mg, about 350 mg, about 400 mg, etc.; similarly, i.v. dosages may be greater than about 10 mg/kg, e.g., about 11 mg/kg, 12 mg/kg, 15 mg/kg, 20 mg/kg, 25 mg/kg, 30 mg/kg, 35 mg/kg, etc. It will also be understood that dose reduction may also be required (e.g., during the induction and/or maintenance phase) for certain patients, e.g., patients that display adverse events or an adverse response to treatment with the IL-17 antagonist (e.g., secukinumab). Thus, dosages of secukinumab may be less than about 75 mg to about 300 mg s.c., e.g., about 25 mg, about 50 mg, about 80 mg, about 100 mg, about 125 mg, about 175 mg, about 200 mg, 250 mg, etc.; similarly, i.v. dosages may be less than about 10 mg/kg, e.g., about 9 mg/kg, 8 mg/kg, 5 mg/kg, 4 mg/kg, 3 mg/kg, 2 mg/kg, 1 mg/kg etc. In some embodiments, the IL-17 antagonist, e.g., IL-17 binding molecule (e.g., IL-17 antibody or antigen-binding fragment thereof, e.g., secukinumab) or IL-17 receptor binding molecule (e.g., IL-17 receptor antibody or antigen-binding fragment thereof) may be administered to the patient at an initial dose, e.g., of 75 mg or 150 mg delivered s.c., and the dose is then escalated to 150 mg or 300 mg if needed, as determined by a physician.

In some embodiments, the dose employed will be dictated by the particular patient. For example, in some embodiments, patients with concomitant moderate-to-severe plaque psoriasis, who previously failed treatment with a biological (e.g., a TNF alpha antagonist), or who previously responded inadequately to a biological (e.g., a TNF alpha antagonist) are preferably administered a 300 mg dose of the IL-17 antibody (e.g. secukinumab).

The timing of dosing is generally measured from the day of the first dose of secukinumab (which is also known as "baseline"). However, health care providers often use different naming conventions to identify dosing schedules, as shown in Table 2.

TABLE 2

Common naming conventions for dosing regimens. Bolded items refer to the naming convention used herein.

| | Week | | | | | | | | | | | |
|---|---|---|---|---|---|---|---|---|---|---|---|---|
| | 0/1 | 1/2 | 2/3 | 3/4 | 4/5 | 5/6 | 6/7 | 7/8 | 8/9 | 9/10 | 10/11 | etc |
| 1$^{st}$ day of week | 0/1 | 7/8 | 14/15 | 21/22 | 28/29 | 35/36 | 42/43 | 49/50 | 56/57 | 63/64 | 70/71 | etc. |

Notably, week zero may be referred to as week one by some health care providers, while day zero may be referred to as day one by some health care providers. Thus, it is possible that different physicians will designate, e.g., a dose as being given during week 3/on day 21, during week 3/on day 22, during week 4/on day 21, during week 4/on day 22, while referring to the same dosing schedule. For consistency, the first week of dosing will be referred to herein as week 0, while the first day of dosing will be referred to as day 1. However, it will be understood by a skilled artisan that this naming convention is simply used for consistency and should not be construed as limiting, i.e., weekly dosing is the provision of a weekly dose of the IL-17 antibody regardless of whether the physician refers to a particular week as "week 1" or "week 2". Moreover, in a preferred dosing regimen, the antibody is administered during week 0, 1, 2, 3, 4 8, 12, 16, 20, etc. Some providers may refer to this regimen as administration of the antibody weekly for five weeks and then monthly (or every 4 weeks) thereafter, beginning during week 8, while others may refer to this regimen as administration of the antibody weekly for four weeks and then monthly (or every 4 weeks) thereafter, beginning during week 4. It will be appreciated by a skilled artisan that this different naming convention nevertheless identifies the same regimen. Ot will be appreciated by a skilled artisan that weekly dosing during week 0, 1, 2, 3, and 4 followed by dosing every 4 weeks is the same regimen as weekly dosing during week 0, 1, 2, and 3, followed by dosing every 4 weeks, beginning during week 4.

Accordingly, disclosed herein are methods of inhibiting the progression of structural damage in a PsA patient, comprising administering an IL-17 antagonist to a patient in need thereof. Also disclosed herein are methods of reducing signs and symptoms of active PsA in a PsA patient, inhibiting the progression of structural (e.g., bone and/or joint) damage in a PsA patient, and improving physical function in a PsA patient, comprising administering an IL-17 antagonist to a patient in need thereof. In some embodiments of the above methods, the patient is biologic-naïve. In some embodiments of the disclosed uses, methods and kits, the patient is biologic-experienced. In some embodiments of the disclosed uses, methods and kits, the patient has not previously been treated with a TNF alpha antagonist. In some embodiments of the disclosed uses, methods and kits, the patient has previously been treated with a TNF alpha antagonist. In some embodiments of the disclosed uses, methods and kits, the patient had an inadequate response to the previous treatment with the TNF alpha antagonist (TNF-inadequate responder (TNF-IR)). In some embodiments of the disclosed uses, methods and kits, inhibition of the progression of structural damage is measured by the van der Heijde psoriatic arthritis-modified total Sharp score (mTSS). In some embodiments of the disclosed uses, methods and kits, inhibition of the progression of structural damage is measured by erosion and joint space narrowing (JSN) scores. In some embodiments of the disclosed uses, methods and kits, the progression of erosion, joint space narrowing, pencil-in-cup phenomena, joint widening, joint narrowing, subluxation, bony proliferation, osteolysis, and/or ankylosis is inhibited. In some embodiments, the disclosed methods further comprise additionally administering the patient a DMARD, e.g., MTX. In some embodiments of the disclosed uses, methods and kits, the IL-17 antagonist is administered to the patient intravenously (i.v.) at about 10 mg/kg every other week during week 0, 2, and 4 and thereafter is administered to the patient subcutaneously (s.c.) at about 75 mg, about 150 mg, or about 300 mg monthly, beginning during week 8. In some embodiments of the disclosed uses, methods and kits, the IL-17 antagonist is administered to the patient s.c. at about 75 mg, about 150 mg, or about 300 mg weekly during weeks 0, 1, 2, and 3, and thereafter is administered to the patient s.c. at about 75 mg, about 150 mg or about 300 mg monthly, beginning during week 4. In some embodiments of the disclosed uses, methods and kits, the patient has concomitant psoriasis. In some embodiments of the disclosed uses, methods and kits, inhibiting the progression of structural damage is defined as a change from baseline in mTSS ≤0.5. In some embodiments of the disclosed uses, methods and kits, inhibiting the progression of structural damage is defined as a change from baseline in erosion score of ≤0.3. In some embodiments of the disclosed uses, methods and kits, inhibiting the progression of structural damage is defined as a change from baseline in JSN score of ≤0.2. In some embodiments, the patient is selected for treatment based on having been previously treated with a TNF alpha antagonist. In some embodiments, the patient is selectively administered the IL-17 antagonist (secukinumab) based on having been previously treated with a TNF alpha antagonist.

In some embodiments of the disclosed uses, methods and kits, the IL-17 antagonist is an IL-17 antibody or antigen-binding fragment thereof. In some embodiments of the disclosed uses, methods and kits, the IL-17 antibody or antigen-binding fragment thereof is selected from the group consisting of: a) an IL-17 antibody or antigen-binding fragment thereof that binds to an epitope of IL-17 comprising Leu74, Tyr85, His86, Met87, Asn88, Val124, Thr125, Pro126, Ile127, Val128, His129; b) an IL-17 antibody or antigen-binding fragment thereof that binds to an epitope of IL-17 comprising Tyr43, Tyr44, Arg46, Ala79, Asp80; c) an IL-17 antibody or antigen-binding fragment thereof that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain; d) an IL-17 antibody or antigen-binding fragment thereof that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain, wherein the IL-17 antibody or antigen-binding fragment thereof has a $K_D$ of about 100-200 pM, and wherein the IL-17 antibody or antigen-binding fragment thereof has an in vivo half-life of about 23 to about 35 days; and e) an IL-17 antibody or antigen-binding fragment thereof comprising: i) an immunoglobulin heavy chain variable domain ($V_H$) comprising the amino acid sequence set forth as SEQ ID NO:8; ii) an immunoglobulin light chain variable domain ($V_L$) comprising the amino acid sequence set forth as SEQ ID NO:10; iii) an immunoglobulin $V_H$ domain comprising the amino acid sequence set forth as SEQ ID NO:8 and an immunoglobulin $V_L$ domain comprising the amino acid sequence set forth as SEQ ID NO:10; iv) an immunoglobulin $V_H$ domain comprising the hypervariable regions set forth as SEQ ID NO:1, SEQ ID NO:2, and SEQ ID NO:3; v) an immunoglobulin $V_L$ domain comprising the hypervariable regions set forth as SEQ ID NO:4, SEQ ID NO:5 and SEQ ID NO:6; vi) an immunoglobulin $V_H$ domain comprising the hypervariable regions set forth as SEQ ID NO:11, SEQ ID NO:12 and SEQ ID NO:13; vii) an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6; viii) an immunoglobulin $V_H$ domain comprising the hypervariable regions set forth as SEQ ID NO:11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6; ix) an immunoglobulin light chain comprising the amino acid sequence set forth as SEQ ID NO:14; x) an immunoglobulin heavy chain comprising the amino acid sequence set forth as SEQ ID NO:15; or xi) an immunoglobulin light chain comprising the amino acid sequence set forth as SEQ ID NO:14 and an immunoglobulin heavy chain comprising the amino acid sequence set forth as SEQ ID NO:15. In some embodiments of the disclosed uses, methods and kits, the IL-17 antibody or antigen-binding fragment thereof is secukinumab.

Additionally disclosed herein are methods of inhibiting the progression of structural damage in a PsA patient, comprising administering to the patient about 75 mg-about 300 mg secukinumab monthly, wherein the patient has previously been treated with a TNF alpha antagonist.

Additionally disclosed herein are methods of inhibiting the progression of structural damage in a PsA patient, comprising administering to the patient about 150 mg or about 300 mg secukinumab by subcutaneous injection, with initial dosing at weeks 0, 1, 2, and 3, followed by monthly dosing starting at week 4, wherein the patient has previously been treated with a TNF alpha antagonist.

Additionally disclosed herein are methods of inhibiting the progression of structural damage in a PsA patient, comprising administering to the patient about 10 mg/kg secukinumab by intravenous injection at weeks 0, 2, and 4, and thereafter administering to the patient about 150 mg or about 300 mg secukinumab by subcutaneous injection starting at week 8, wherein the patient has previously been treated with a TNF alpha antagonist.

Additionally disclosed herein are IL-17 antagonists (e.g., secukinumab) for use in the manufacture of a medicament for inhibiting the progression of structural damage in a PsA patient, wherein the PsA patient previously been treated with a TNF alpha antagonist).

Additionally disclosed herein are methods of inhibiting the progression of structural damage in a PsA patient, comprising administering to the patient about 75 mg-about 300 mg secukinumab monthly, wherein the patient is selected for treatment based on having previously been treated with a TNF alpha antagonist.

Additionally disclosed herein are methods of inhibiting the progression of structural damage in a PsA patient, comprising selectively administering to the patient about 75 mg-about 300 mg secukinumab monthly, wherein the patient is selected for treatment based on having previously been treated with a TNF alpha antagonist.

Additionally disclosed herein are IL-17 antagonists (e.g., secukinumab) for use in the manufacture of a medicament for inhibiting the progression of structural damage in a PsA patient (e.g., a PsA patient previously been treated with a TNF alpha antagonist) wherein the medicament is formulated to comprise containers, each container having a sufficient amount of the IL-17 antagonist to allow delivery of at least about 75 mg-about 300 mg (e.g., about 75 mg, about 150 mg, about 300 mg) of the IL-17 antagonist (e.g., secukinumab) per unit dose.

Additionally disclosed herein are IL-17 antagonists (e.g., secukinumab) for use in the manufacture of a medicament for inhibiting the progression of structural damage in a PsA patient (e.g., a patient previously treated with a TNF alpha antagonist) wherein the medicament is formulated to comprise containers, each container having a sufficient amount of the IL-17 antagonist to allow subcutaneous delivery of at least about 75 mg-about 300 mg (e.g., about 75 mg, about 150 mg, about 300 mg) IL-17 antagonist (e.g., secukinumab) per unit dose.

Additionally disclosed herein are IL-17 antagonists (e.g., secukinumab) for use in the manufacture of a medicament for inhibiting the progression of structural damage in a PsA patient (e.g., a patient who previously treated with a TNF alpha antagonist) wherein the medicament is formulated to comprise containers, each container having a sufficient amount of the IL-17 antagonist to allow delivery of at least about 10 mg/kg per unit dose.

Additionally disclosed herein are IL-17 antagonists (e.g., secukinumab) for use in the manufacture of a medicament for inhibiting the progression of structural damage in a PsA patient (e.g., a patient previously treated with a TNF alpha antagonist), wherein the medicament is formulated at a dosage to allow intravenous delivery of about 10 mg/kg per unit dose.

As used herein, the phrase "formulated at a dosage to allow [route of administration] delivery of [a designated dose]" is used to mean that a given pharmaceutical composition can be used to provide a desired dose of an IL-17 antagonist, e.g., an IL-17 antibody, e.g., secukinumab, via a designated route of administration (e.g., s.c. or i.v.). As an example, if a desired subcutaneous dose is 300 mg, then a clinician may use 2 ml of an IL-17 antibody formulation having a concentration of 150 mg/ml, 1 ml of an IL-17 antibody formulation having a concentration of 300 mg/ml, 0.5 ml of an IL-17 antibody formulation having a concentration of 600 mg/ml, etc. In each such case, these IL-17 antibody formulations are at a concentration high enough to allow subcutaneous delivery of the IL-17 antibody. Subcutaneous delivery typically requires delivery of volumes of less than about 2 ml, preferably a volume of about 1 ml or less.

As used herein, "container having a sufficient amount of the IL-17 antagonist to allow delivery of [a designated dose]" means that a given container (e.g., vial, pen, syringe) has disposed therein a volume of an IL-17 antagonist (e.g., as part of a pharmaceutical composition) that can be used to provide a desired dose. As an example, if a desired dose is 150 mg, then a clinician may use 2 ml from a container (e.g., pre-filled syringe or autoinjector) that contains an IL-17 antibody formulation with a concentration of 75 mg/ml, 1 ml from a container (e.g., pre-filled syringe or autoinjector) that contains an IL-17 antibody formulation with a concentration of 150 mg/ml, 0.5 ml from a container (e.g., pre-filled syringe or autoinjector) contains an IL-17 antibody formulation with a concentration of 300 mg/ml, etc. In each such case, these containers (e.g., pre-filled syringe or autoinjector) have a sufficient amount of the IL-17 antagonist to allow delivery of the desired 150 mg dose.

Disclosed herein are IL-17 antagonists (e.g., secukinumab) for the manufacture of a medicament for the treatment of PsA in a patient, wherein the medicament is formulated to comprise containers, each container having a sufficient amount of the IL-17 antagonist to allow delivery of at least about 150 mg-about 300 mg IL-17 antagonist (e.g., secukinumab) per unit dose.

Disclosed herein are IL-17 antagonists (e.g., secukinumab) for the manufacture of a medicament for the treatment of PsA in a patient, wherein the medicament is formulated to comprise containers, each container having a sufficient amount of the IL-17 antagonist (e.g., secukinumab) to allow delivery of at least about 10 mg/kg per unit dose.

Disclosed herein are IL-17 antagonists (e.g., secukinumab) for the manufacture of a medicament for the treatment of PsA in a patient, wherein the medicament is formulated at a dosage to allow intravenous delivery of about 10 mg/kg per unit dose.

Disclosed herein are IL-17 antagonists (e.g., secukinumab) for the manufacture of a medicament for the treatment of PsA, wherein the medicament is formulated at a dosage to allow subcutaneous delivery of about 150 mg-about 300 mg IL-17 antagonist per unit dose.

Kits

The disclosure also encompasses kits for preventing structural damage (e.g., bone and joint) in a PsA patient. Such kits comprise an IL-17 antagonist, e.g., IL-17 binding molecule (e.g., IL-17 antibody or antigen-binding fragment thereof, e.g., secukinumab) or IL-17 receptor binding molecule (e.g., IL-17 receptor antibody or antigen-binding fragment thereof) (e.g., in liquid or lyophilized form) or a pharmaceutical composition comprising the IL-17 antagonist (described supra). Additionally, such kits may comprise means for administering the IL-17 antagonist (e.g., an autoinjector, a syringe and vial, a prefilled syringe, a prefilled pen) and instructions for use. These kits may contain additional therapeutic agents (described supra) for treating PsA, e.g., for delivery in combination with the enclosed IL-17 antagonist, e.g., IL-17 binding molecule, e.g., IL-17 antibody, e.g., secukinumab. Such kits may also comprise instructions for administration of the IL-17 antagonist (e.g., IL-17 antibody, e.g., secukinumab) to inhibit the progression of structural damage in PsA patients (e.g., TNF-naïve and/or TNF-IR PsA patients). Such instructions may provide the dose (e.g., 10 mg/kg, 75 mg, 150 mg, 300 mg), route of administration (e.g., i.v. or s.c.), and dosing regimen (e.g., about 10 mg/kg given i.v., every other week during weeks 0, 2, and 4, and thereafter at about 75 mg, about 150 mg, or about 300 mg given s.c. monthly, beginning during week 8; or about 75 mg, about 150 mg, or about 300 mg given s.c. weekly during week 0, 1, 2, and 3 and thereafter at about 75 mg, about 150 mg, or about 300 mg given s.c. monthly, beginning during week 4) for use with the enclosed IL-17 antagonist, e.g., IL-17 binding molecule, e.g., IL-17 antibody, e.g., secukinumab.

The phrase "means for administering" is used to indicate any available implement or container for systemically administering a drug to a patient, including, but not limited to, a pre-filled syringe, a vial and syringe, an injection pen, an autoinjector (e.g., having a syringe therein), an i.v. drip and bag, a pump, etc. With such items, a patient may self-administer the drug (i.e., administer the drug on their own behalf) or a physician may administer the drug.

Disclosed herein are kits for use in inhibiting the progression of structural damage in a PsA patient, comprising an IL-17 antagonist (e.g., IL-17 binding molecule, e.g., IL-17 antibody or antigen-binding fragment thereof, e.g., secukinumab). In some embodiments, the kit further comprises means for administering the IL-17 antagonist to the patient. In some embodiments, the kit further comprises instructions for administration of the IL-17 antagonist, wherein the instructions indicate that the IL-17 antagonist (e.g., IL-17 binding molecule, e.g., IL-17 antibody or antigen-binding fragment thereof, e.g., secukinumab) is to be administered to the patient (e.g., TNF naive and/or TNF experienced) intravenously (i.v.) at about 10 mg/kg every other week during week 0, 2, and 4 and thereafter is to be administered to the patient subcutaneously (s.c.) at about 75 mg-about 300 mg (e.g., about 75 mg, about 150 mg, or about 300 mg) monthly, beginning during week 8. In some embodiments, the kit further comprises instructions for administration of the IL-17 antagonist, wherein the instructions indicate that the IL-17 antagonist (e.g., IL-17 binding molecule, e.g., IL-17 antibody or antigen-binding fragment thereof, e.g., secukinumab) is to be administered the patient s.c. at about 75 mg-about 300 mg (e.g., about 75 mg, about 150 mg, or about 300 mg) weekly during weeks 0, 1, 2, and 3, and thereafter is to be administered to the patient s.c. at about 75 mg-about 300 mg (e.g., about 75 mg, about 150 mg, or about 300 mg) monthly, beginning during week 4.

General

In preferred embodiments of the disclosed methods, treatments, regimens, uses and kits, the IL-17 antagonist is an IL-17 binding molecule. In preferred embodiments, the IL-17 binding molecule is an IL-17 antibody or antigen-binding fragment thereof. In preferred embodiments of the disclosed methods, treatments, regimens, uses and kits, the IL-17 antibody or antigen-binding fragment thereof is selected from the group consisting of: a) an IL-17 antibody or antigen-binding fragment thereof that binds to an epitope of IL-17 comprising Leu74, Tyr85, His86, Met87, Asn88, Val124, Thr125, Pro126, Ile127, Val128, His129; b) an IL-17 antibody or antigen-binding fragment thereof that binds to an epitope of IL-17 comprising Tyr43, Tyr44, Arg46, Ala79, Asp80; c) an IL-17 antibody or antigen-binding fragment thereof that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain; d) an IL-17 antibody or antigen-binding fragment thereof that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain, wherein the IL-17 binding molecule has a $K_D$ of about 100-200 pM, and wherein the IL-17 binding molecule has an in vivo half-life of about 23 to about 35 days; and e) an IL-17 antibody or antigen-binding fragment thereof comprising: i) an immunoglobulin (Ig) heavy chain variable domain ($V_H$) comprising the amino acid sequence set forth as SEQ ID NO:8; ii) an Ig light chain variable domain ($V_L$) comprising the amino acid sequence set forth as SEQ ID NO:10; iii) an Ig $V_H$ domain comprising the amino acid sequence set forth as SEQ ID NO:8 and an Ig $V_L$ domain comprising the amino acid sequence set forth as SEQ ID NO:10; iv) an Ig $V_H$ domain comprising the hypervariable regions set forth as SEQ ID NO:1, SEQ ID NO:2, and SEQ ID NO:3; v) an Ig $V_L$ domain comprising the hypervariable regions set forth as SEQ ID NO:4, SEQ ID NO:5 and SEQ ID NO:6; vi) an Ig $V_H$ domain comprising the hypervariable regions set forth as SEQ ID NO:11, SEQ ID NO:12 and SEQ ID NO:13; vii) an Ig $V_H$ domain comprising the hypervariable regions set forth as SEQ ID NO:1, SEQ ID NO:2, and SEQ ID NO:3 and an Ig $V_L$ domain comprising the hypervariable regions set forth as SEQ ID NO:4, SEQ ID NO:5 and SEQ ID NO:6; viii) an Ig $V_H$ domain comprising the hypervariable regions set forth as SEQ ID NO:11, SEQ ID NO:12 and SEQ ID NO:13 and an Ig $V_L$ domain comprising the hypervariable regions set forth as SEQ ID NO:4, SEQ ID NO:5 and SEQ ID NO:6; ix) an Ig light chain comprising the amino acid sequence set forth as SEQ ID NO:14; x) an Ig heavy chain comprising the amino acid sequence set forth as SEQ ID NO:15; or xi) an Ig light chain comprising the amino acid sequence set forth as SEQ ID NO:14 and an Ig heavy chain comprising the amino acid sequence set forth as SEQ ID NO:15.

In preferred embodiments of the disclosed uses, methods and kits, the IL-17 antibody or antigen-binding fragment thereof is a human antibody of the $IgG_1$ isotype. In preferred embodiments, the antibody or antigen-binding fragment thereof is secukinumab. In preferred embodiments, the IL-17 antibody, e.g., secukinumab, is administered as a liquid pharmaceutical composition (e.g., reconstituted from a lyophilisate or not reconstituted from a lyophilisate The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference. The following Examples are presented in order to more fully illustrate the preferred embodiments of the disclosure. These examples should in no way be construed as limiting the scope of the disclosed patient matter, as defined by the appended claims.

EXAMPLES

Example 1

Proof of Concept PsA Trial CAIN4572206

Example 1.1

Study Design CAIN4572206

This was a randomized, double-blind, placebo controlled, multi-center proof of concept study of multiple doses (2 infusions 3 weeks apart) of 10 mg/kg AIN457 for the treatment of patients with a diagnosis of active PsA based on currently advocated classification criteria for clinical trials (CASPAR). Patients with moderate to severe PsA fulfilling the following criteria were enrolled: (i) CASPAR criteria (Taylor Wet al (2006) Arthritis Rheum 54:2665-73) for a diagnosis of psoriatic arthritis; with the modification that swelling and tenderness of at least three peripheral joints, (ii) PGA ≥40, (iii) inflammatory pain ≥40; (iv) disease is inadequately controlled on least one DMARD given for at least three months at the maximum tolerated dose (v) RF ≤100 IU AND negative CCP ELISA test. Efficacy evaluations were based on the following qualified assessment domains in accordance with the OMERACT 8 consensus: 1. peripheral joint involvement (ACR response criteria with 68/68 joint count, PsARC (Clegg et al (1996) Arthritis Rheum 39:2013-20) with DIP joints to be included in the joint count, i.e. 78/76 joint count); DAS28; 2. skin assessment (PASI score) (Feldman and Krueger (2005) Ann. Rheum. Dis. 64:ii65-ii68); 3. pain (VAS); 4. function: SF36 physical component; 5. patient global assessment by VAS (PGA); and 6. HAQ Tender 78-Joint Count and Swollen 76-Joint Count The distal interphalangeal joints of the feet and carpometacarpal joints of the hands were added to the usual ACR joint count of 68 tender and 66 swollen joints, to yield a 78 and 76 joint count, respectively. Thus, the joints assessed for tenderness included the distal interphalangeal, proximal interphalangeal and metacarpophalangeal joints of the hands, and metatarsophalangeal joints of the feet, the carpometacarpal and wrist joints (counted separately), the elbows, shoulders, acromioclavicular, sternoclavicular, hip, knee, talo-tibial, and mid-tarsal joints. All of these except for the hips are assessed for swelling. Joint tenderness and swelling to be graded present (1) or absent (0). The other individual elements in the ACR scoring system, VAS scores of patient pain, patient global, physician global, the Health Assessment Questionnaire (HAQ), and acute phase reactant, C-reactive protein (CRP) or erythrocyte sedimentation rate (ESR) are unchanged from the way they are used in standard trials of rheumatoid arthritis. To achieve an ACR 20, 50, or 70 response, at least 20%, 50%, or 70%, respectively, improvement in tender and swollen joint counts and three of five scores of individual elements (VAS scores of patient pain, physician and patient global assessment, a disability measure (HAQ) and an acute phase reactant (ESR or CRP)).

In addition to ACR and PsARC, DAS28 is calculated based on assessments of the following 28 joints for tenderness and swelling: metacarpophalangeal I-V (10), thumb interphalangeal (2), hand proximal interphalangeal II-V (8), wrist (2), elbow (2), shoulders (2), and knees (2).

ACR20, ACR50, ACR70 Responder Definitions

A subject is defined as an ACR20 responder if, and only if, the following three conditions hold: 1. they have a ≥20% improvement in the number of tender joints (based on 68 joints); 2. they have a ≥20% improvement in the number of swollen joints (based on 66 joints); 3. they have a ≥20% improvement in three of the following five domains:

Patient Global Assessment (measured on a VAS scale, 0-100)

Physician Global Assessment (measured on a VAS scale, 0-100)

Pain (measured on a VAS scale, 0-100)

Disability (as measured by the Health Assessment Questionnaire)

Acute phase reactant (as measured by CRP)

ACR50 and ACR70 responders are defined in a similar manner with improvements of ≥50% and ≥70% respectively.

PsARC Responder Definition

A subject is defined as a PsARC responder if, and only if, they have an improvement in two of the following four factors (with at least one factor being a joint count) and no worsening in the remaining factors Patient global assessment (0-100 VAS scale, improvement defined as decrease of at least 20 units)

Physician global assessment (0-100 VAS scale, improvement defined as decrease of at least 20 units)

Tender 78-joint count (improvement defined as decrease of at least 30%)

Swollen 76-joint count (improvement defined as decrease of at least 30%)

The proportion of subjects that meet each of the four responder definitions will be summarized by treatment group and time-point. Plots of these proportions over time will be presented.

DAS28 Score

The DAS28 score will be derived using the following formula:

$$DAS28 = 0.56 * \sqrt{(tender28)} + 0.28\sqrt{(swollen28)} + 0.36 * \log_e(CRP+1) + 0.014 * GH + 0.96,$$ where tender28=Tender Joint Count (based on 28 joints), swollen28=Swollen Joint Count (based on 28 joints), CRP=C-reactive protein (measured in mg/L), and GH=Patients Global Assessment (measured on a VAS scale, 0-100)

Patient's Assessment of Pain Intensity

The patient's assessment of pain was performed using 100 mm VAS ranging from no pain to unbearable pain. At the investigator's site the distance in mm from the left edge of the scale was measured and the value entered on the eCRF.

Patient's Global Assessment of Disease Activity

The patient's global assessment of disease activity was performed using 100 mm VAS ranging from not severe to very severe, after the question "In the past week how severely was your overall health affected". At the investigator's site the distance in mm from the left edge of the scale was measured and the value entered on the eCRF.

Physician's Global Assessment of Disease Activity

The physician's global assessment of disease activity was performed using 100 mm VAS ranging from no disease activity to maximal disease activity, after the question "Considering all the ways the disease affects your patient, draw a line on the scale for how well his or her condition is today". To enhance objectivity, the physician must not be aware of the specific patient's global assessment of disease activity, when performing his own assessment on that patient. The investigator then measured the distance in mm from the left edge of the scale and the value entered on the eCRF.

C-Reactive Protein (CRP)

Blood for this assessment was obtained in order to identify the presence of inflammation, to determine its severity, and to monitor response to treatment. Since the results of this test may unblind study personnel, results from the central lab will be provided for screening and baseline only. CRP results from samples collected during the treatment period were revealed following database lock only.

Erythrocyte Sedimentation Rate (ESR)

Blood was obtained to measure ESR, which is helpful in diagnosing inflammatory diseases and is used to monitor disease activity and response to therapy. ESR was measured locally using a standard kit supplied by the central lab.

Disease Activity Score 28 (DAS28) and Patients in Remission

The DAS28 will be conducted according to the assessment schedule as described (Aletaha D, Smolen J (2005). Clin.Exp.Rheumatol; 23 (5 Suppl 39): S100-S108; Aletaha et al (2005). Arthritis Rheum.; 52 (9):2625-36). The percentage of patients in remission (DAS28≤2.6) was determined at weeks 6 and 24/end of study.

Mastricht Ankylosing Spondylitis Enthesis Score (MASES)

The Mastricht Ankylosing Spondylists Enthesis Score (MASES) (Heuft-Dorenbosch L, et al (2003) Ann Rheum Dis 62:127-32; Gladman D D (2007) Curr Rheumatol Rep 9:455-60) was developed from the Mander index, and includes assessments of 13 sites. Enthesitis sites included in the MASES index are: 1st costochondral, 7$^{th}$ costochondral, posterior superior iliac spine, anterior superior iliac spine, iliac crest (all above assessed bilaterally), 5th lumbar spinous process, proximal Achilles (bilateral).

SPARCC (SpA Research Consortium of Canada)

SPARCC (SpA Research Consortium of Canada) (Maksymowych et al. (2003) J. Rheumatology 30:1356-63) evaluates 18 enthesis sites: medial and lateral epicondyle humerus, supraspinatus insertion, proximal Achilles, greater trochanter, medial and lateral condyl femur, insertion of plantar fascia, quadriceps insertion of patella, inferior pole of patella, tibial tubercle.

Leeds Dactylitis Instrument (LDI)

The Leeds Dactylitis Instrument (LDI) (Helliwell et al (2005). J Rheumatol 32:1745-50) basic measures the ratio of the circumference of the affected digit to the circumference of the digit on the opposite hand or foot, using a minimum difference of 10% to define a dactylitic digit. The ratio of circumference is multiplied by a tenderness score, using a modification of LDI which is a binary score (1 for tender, 0 for non-tender). If both sides are considered involved, the number will be compared to data provided in a table. This modification is referred to as LDI basic and will be applied in this study. The LDI requires a tool to measure digital circumference (available from www.rehaboutlet.com, Miami, Fla., USA).

Psoriasis Area and Severity Index (PASI)

The PASI (Feldman and Krueger (2005) Ann. Rheum. Dis. 64:ii65-ii68) assesses the extent of psoriasis on four body surface areas (head, trunk and upper and lower limbs) and the degree of plaque erythema, scaling and thickness. The PASI score accounts for the extent of body surface area affected by the erythema, scaling and thickness and the severity of these measures. The score ranges from 0 (no disease) to 72 (maximal disease).

Example 1.2

Secukinumab Improves Signs and Symptoms of PsA

CAIN4572206 assessed the safety and preliminary efficacy of secukinumab inhibiting Interleukin-17A, a novel target for the treatment of PsA. 42 patients with active PsA who fulfilled CASPAR criteria were randomized 2:1 to receive two injections of secukinumab (10 mg/kg) or placebo, given 3 weeks apart. The primary efficacy endpoint was the proportion of ACR20 responders at Week 6 in active versus placebo (one-sided p<0.01). 35 (83.3%) patients (25 on secukinumab, 10 on placebo) completed the study. 5 patients (4 secukinumab and 1 placebo) were excluded from the efficacy analysis due to protocol violations and 7 (3 secukinumab and 4 placebo) discontinued prematurely for lack of efficacy or withdrawal of consent. Demographics and baseline characteristics were balanced between groups including parameters: mean±SD SJC (secukinumab vs. placebo): 8.3±5.6 vs. 9.5±5.4; TJC 23.5±19.4 vs. 22.6±11.0; DAS284.8±1.2 vs. 4.8±1.2; MASES 3.0±4.1 vs. 3.4±2.3. Co-existing psoriasis, prior TNFi exposure and co-medication with DMARDS were present in 23, 11 and 21 patients on secukinumab and in 11, 5 and 10 on placebo, respectively. ACR20 responders on secukinumab vs. placebo were 39% vs. 23% (P=0.27) at Week 6, 39% vs. 15% at Week 12, 43% vs. 18% at Week 28. ACR50 and ACR70 responders on secukinumab vs. placebo were 17% vs. 8% and 9% vs. 0%, respectively at Week 6. CRP reductions at Week 6 were greater on secukinumab (median [range] at baseline vs. Week 6: 4.9 [0.3, 43.0] vs. 3.0 [0.2, 15.2]) than on placebo (6.2 [1.3, 39.7] vs. 5.0 [0.8, 29.6]).

Overall rate of adverse events (AEs) was comparable in secukinumab 26 (93%) vs. placebo 11 (79%). 7 serious AEs were reported in 4 secukinumab patients and 1 in placebo. Infections were reported in 16 (57%) patients on secukinumab and 7 (50%) on placebo. In conclusion, the primary endpoint was not met, though patients showed rapid and sustained improvements of clinical scores and CRP levels up to Week 28. The safety profile of secukinumab was favorable.

Example 2

Secukinumab Results of AIN457F2306 (FUTURE 1) Trial in PsA

Example 2.1

Summary of FUTURE 1

In this double-blind, phase 3 study, 606 subjects were randomized (1:1:1) to i.v. secukinumab 10 mg/kg (Weeks 0, 2, 4) followed by s.c. secukinumab 150 mg (secukinumab 10 mg/kg i.v. →150 mg s.c.) or 75 mg (secukinumab 10 mg/kg i.v. →75 mg s.c) every 4 weeks, or placebo on the same administration schedule. The primary end point was a 20% improvement in the American College of Rheumatology response criteria (ACR 20) at Week 24.

ACR 20 response rates at Week 24 were significantly higher with secukinumab 10 mg/kg i.v. →150 mg s.c (50.0%) and secukinumab 10 mg/kg i.v. →75 mg s.c (50.5%) versus placebo (17.3%; P<0.001), with significant improvements observed as early as Week 1. ACR 50 and ACR 70 response rates were also higher with secukinumab. Improvements were observed in both biologic-naïve subjects and those with previous inadequate response to biologics. Secukinumab significantly inhibited radiographic disease progression at Week 24 compared with placebo (P<0.05). Significant improvements with secukinumab at Week 24 were also observed for skin psoriasis, enthesitis, dactylitis, disease activity score, physical functioning and quality of life. Improvements were sustained through Week 52. Secukinumab was generally well tolerated with no unexpected safety findings.

Secukinumab provided rapid, significant and sustained improvements in key clinical domains of psoriatic arthritis, including radiographic progression, validating interleukin-17A as a therapeutic target in this disease setting.

Example 2.2

Detailed Discussion of FUTURE 1

Subjects were aged 18 years or older, with a diagnosis of psoriatic arthritis according to the Classification Criteria for Psoriatic Arthritis [CASPAR] (Taylor et al. (2006) Arthritis Rheum 2006; 38:727-35) and active disease, defined as having 3 or more tender joints and 3 or more swollen joints, despite treatment with nonsteroidal anti-inflammatory drugs, disease modifying antirheumatic drugs and/or TNF inhibitors. Concomitant oral corticosteroids (≤10 mg per day prednisone or equivalent) and methotrexate (≤25 mg per week) were permitted provided the dose was stable. Subjects who had previously received a TNF inhibitor (biologic-experienced) must have experienced an inadequate response or stopped treatment due to safety or tolerability reasons.

Key exclusion criteria included: prior therapy with biologic immunomodulating agents other than TNF inhibitors; treatment with more than 3 different TNF inhibitors; active inflammatory diseases other than psoriatic arthritis; active infection in the 2 weeks prior to randomization, or a history of ongoing, chronic or recurrent infections.

After a 4-week screening period, subjects were randomized in a 1:1:1 ratio to one of two secukinumab treatment groups or placebo. The study design in shown in FIG. 1. Secukinumab–treated subjects received an intravenous dose of 10 mg/kg at baseline (Week 0) and at Weeks 2 and 4, followed by subcutaneous secukinumab 150 mg (secukinumab 10 mg/kg i.v. →150 mg s.c.) or 75 mg (secukinumab 10 mg/kg i.v. →75 mg s.c.) administered every 4 weeks thereafter; subjects in the placebo group were treated according to the same intravenous and subcutaneous dosing schedules. At Week 16, all subjects were classified (in a blinded manner) as responders, defined as at least a 20% improvement from baseline in tender and swollen joint counts, or nonresponders. Subjects treated with placebo were re-randomized (1:1) to receive subcutaneous secukinumab 150 mg or 75 mg every 4 weeks from either Week 16 (nonresponders) or Week 24 (responders). Subjects were stratified according to prior TNF inhibitor exposure; approximately 70% of subjects were required to be biologic-naive.

Efficacy and safety assessments were performed at each study visit through Week 52. The primary efficacy endpoint was the proportion of subjects achieving a 20% improvement in the American College of Rheumatology response criteria (ACR 20; Felson et al. Arthritis Rheum 1995; 38:727-35) at Week 24. Secondary efficacy evaluations at Week 24 included: ACR 50 response; 75% and 90% improvement in Psoriasis Area-and-Severity Index score (PASI 75 and PASI 90; Weisman et al. J Dermatolog Treat. 2003; 14:158-65) amongst the subgroup of subjects with at least 3% body surface area affected by psoriasis at baseline; presence of dactylitis (assessed by dactylitic joint count) andenthesitis (assessed by a four-point enthesitis index) amongst subjects with these characteristics at baseline; change from baseline in 28-joint Disease Activity Score using C-reactive protein (DAS28-CRP; Wells et al. Ann Rehum Dis 2009; 68:954-60); quality of life assessed using the Medical Outcomes Study 36-Item Short-Form Health Survey (SF-36) version 2 [Ware et al. Med Care 1992; 30:473-83]; physical function assessed using the Health Assessment Questionnaire Disability Index (HAQ-DI; Fries et al. Arthritis Rheum 1980:23:137-45). Radiographic progression was assessed using the van der Heijde psoriatic arthritis-modified total Sharp score (mTSS, vdH-mTSS; van der Heijde et al. Arthritis Rheum 2005; 52:49-60). Radiographic evaluations of the hands/wrists and feet were performed at baseline, Week 16 or 24 (depending on response) and Week 52. Images were scored centrally by two independent readers. Exploratory efficacy evaluations included ACR70 response rates and radiographic assessment of erosions and joint space narrowing at Week 24, and the evaluation of each efficacy end point over time and beyond Week 24. Pre-specified subgroup analyses on the basis of previous biologic therapy were performed for key efficacy end points. Several other exploratory assessments, including pharmacokinetic measurements, were conducted but are not described herein.

Safety was evaluated by assessing adverse events, serious adverse events, and routine hematologic and laboratory values. The National Cancer Institute's Common Terminology Criteria for Adverse Events, version 4.0, was used to grade the severity of adverse events. Potential major adverse cardiac events were adjudicated by an independent expert committee.

A sample size of 600 subjects was estimated to have 99% power to detect a 27% improvement in ACR 20 response rates at a two-sided, type I error alpha of 0.05. For efficacy assessments at Week 24, statistical analyses used non-responder imputation for binary variables, mixed-effects repeated measures model for continuous variables, and linear extrapolation for radiographic data, following a pre-defined hierarchical hypothesis testing strategy to adjust for multiplicity. Observed data are reported after Week 24 unless otherwise indicated. Safety analyses included all subjects randomized into the study who received at least one dose of a study drug.

A total of 817 subjects were screened, of whom 606 underwent randomization (n=202 per study arm); 553 (91.3%) subjects completed the 24-week evaluation period and 515 (85.0%) completed the 52-week study period.

Baseline demographics, disease characteristics and prior or concomitant medication usage were similar across study groups (Table 3). Approximately half (53.6%) of randomized subjects had psoriasis affecting at least 3% of their body surface area, 53.4% had dactylitis and 61.4% had enthesitis. Approximately two-thirds (70.5%) of subjects were biologic-naive and 59.4% were receiving concomitant methotrexate.

Figure 2C:
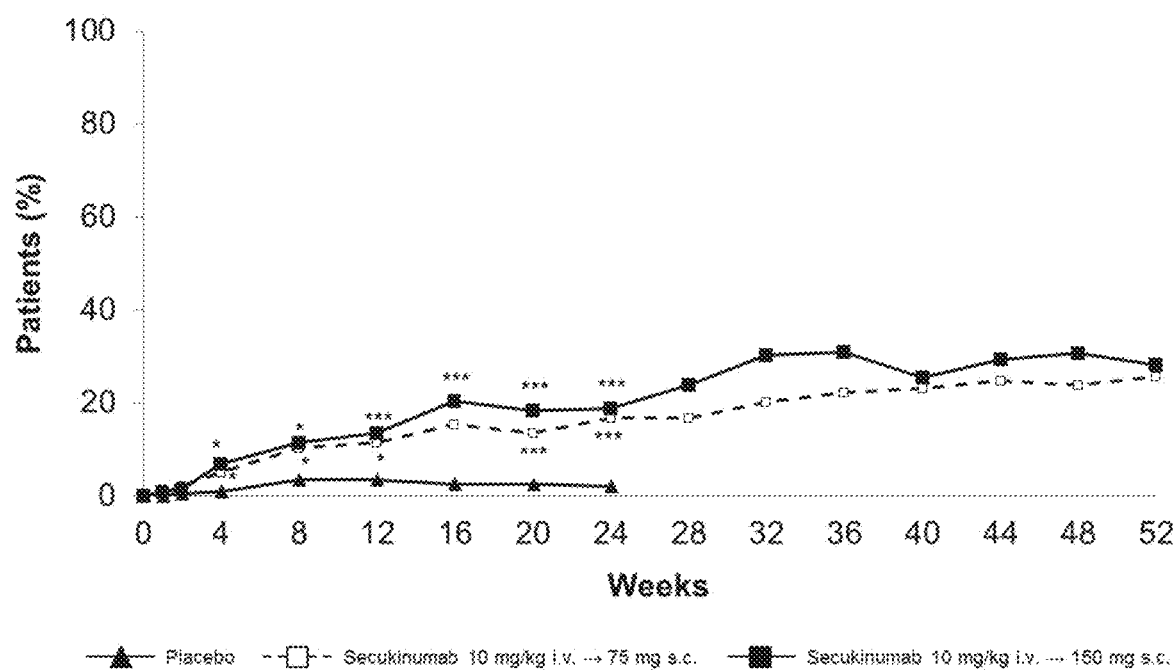

At Week 24, a higher proportion of subjects receiving secukinumab 10 mg/kg i.v. →150 mg s.c and secukinumab 10 mg/kg i.v. →75 mg s.c. achieved an ACR 20 response compared with placebo (50.0% and 50.5% versus 17.3%;

P<0.001; Table 4), with significant improvements observed as early as Week 1. ACR 50 and ACR 70 response rates were also significantly higher with secukinumab versus placebo at Week 24 (Table 4; FIG. 2). Significant improvements with both doses of secukinumab versus placebo were observed for all other pre-specified secondary endpoints at Week 24, including PASI 75 and PASI 90 responses, change from baseline in DAS28-CRP, SF-36 physical component score and HAQ-DI score, and the proportion of subjects with dactylitis and enthesitis (Table 4). There were no significant differences in terms of clinical responses between secukinumab doses up to Week 24.

TABLE 3

Subject Demographics and Disease Characteristics at Baseline.

| Characteristic | Secukinumab 10 mg/kg i.v. → 150 mg s.c. (N = 202) | Secukinumab 10 mg/kg i.v. → 75 mg s.c. (N = 202) | Placebo (N = 202) |
|---|---|---|---|
| Age in years, mean (SD) | 49.6 (11.8) | 48.8 (12.2) | 48.5 (11.2) |
| Female sex, n (%) | 106 (52.5) | 118 (58.4) | 106 (52.5) |
| Weight in kg, mean (SD) | 84.2 (21.1) | 84.5 (19.6) | 80.0 (20.5) |
| Race, n (%) | | | |
| White | 162 (80.2) | 165 (81.7) | 154 (76.2) |
| Black | 3 (1.5) | 2 (1.0) | 0 |
| Asian | 36 (17.8) | 33 (16.3) | 46 (22.8) |
| Other | 1 (0.5) | 1 (0.5) | 2 (1.0) |
| Unknown | 0 | 1 (0.5) | 0 |
| Number of prior TNF inhibitors, n (%) | | | |
| 0 | 143 (70.8) | 142 (70.3) | 142 (70.3) |
| 1 | 39 (19.3) | 35 (17.3) | 36 (17.8)* |
| ≥2 | 20 (9.9) | 25 (12.4) | 24 (11.9) |
| Methotrexate use at randomization, n (%) | 118 (58.4) | 118 (58.4) | 124 (61.4) |
| Systemic glucocorticoid use at randomization, n (%) | 34 (16.8) | 34 (16.8) | 27 (13.4) |
| Subjects with specific disease characteristics, n (%) | | | |
| Psoriasis BSA ≥3% | 108 (53.5) | 108 (53.5) | 109 (54.0) |
| PASI score ≤10 | 141 (69.8) | 155 (76.6) | 136 (67.3) |
| Dactylitis | 104 (51.5) | 104 (51.5) | 116 (57.4) |
| Enthesitis | 126 (62.4) | 129 (63.9) | 117 (57.9) |
| Baseline disease and quality of life scores, mean (SD) | | | |
| TJC (78 joints) | 23.8 (16.4) | 23.4 (17.2) | 25.1 (18.4) |
| SJC (76 joints) | 12.5 (9.4) | 12.7 (11.1) | 14.9 (13.1) |
| DAS28-CRP | 4.8 (1.1) | 4.9 (1.2) | 4.9 (1.1) |
| PASI | 9.2 (12.5) | 6.4 (8.0) | 8.9 (11.0) |
| PGA | 58.3 (18.9) | 54.3 (18.0) | 56.7 (18.8) |
| HAQ-DI | 1.23 (0.68) | 1.25 (0.67) | 1.19 (0.64) |
| Psoriatic arthritis pain (VAS) | 55.7 (24.2) | 55.1 (22.1) | 56.7 (21.1) |
| Patient's global assessment (VAS) | 55.2 (24.0) | 56.1 (22.6) | 55.6 (21.7) |

*Note,
one subject received one dose of infliximab which was subsequently discontinued for logistical reasons, rather than due to inadequate response. The infliximab dose was recorded as a prior medication, but the subject was reported as biologic-naïve.
BSA, body surface area;
DAS28-CRP, 28-joint Disease Activity Score based on C-reactive protein;
HAQ-DI, health assessment questionnaire disability index;
PASI, psoriasis area-and-severity index;
PGA, physician's global assessment;
PsA, psoriatic arthritis; SD, standard deviation;
SJC, swollen joint count;
TJC, tender joint count;
TNF, tumor necrosis factor;
VAS, visual analog scale.

TABLE 4

Comparison of Efficacy at Week 24 (Placebo-controlled Phase) Across Several Arthritis, Psoriasis and Patient-reported Outcomes.

| Efficacy endpoint | Secukinumab 10 mg/kg i.v. → 150 mg s.c. | Secukinumab 10 mg/kg i.v. → 75 mg s.c. | Placebo |
|---|---|---|---|
| All subjects (overall population) | | | |
| ACR 20 response, n/N (%) | 101/202 (50.0)*** | 102/202 (50.5)*** | 35/202 (17.3) |
| ACR 50 response, n/N (%) | 70/202 (34.7)*** | 62/202 (30.7)*** | 15/202 (7.4) |
| ACR 70 response, n/N (%) | 38/202 (18.8)*** | 34/202 (16.8)*** | 4/202 (2.0) |
| DAS28-CRP, LS mean change from baseline (SE)† | −1.62 (0.084)*** | −1.67 (0.085)*** | −0.77 (0.123) |
| Subjects with dactylitis, n/N (%) | 54/104 (51.9)*** | 45/104 (43.3)*** | 98/116 (84.5) |
| Subjects with enthesitis, n/N (%) | 68/126 (54.0)*** | 66/129 (51.2)*** | 102/117 (87.2) |
| Joint structural damage (mTSS, vdH-mTSS), mean change from baseline‡ | 0.13* | 0.02* | 0.57 |
| PASI 75 response, n/N (%) | 66/108 (61.1)*** | 70/108 (64.8)*** | 9/109 (8.3) |
| PASI 90 response, n/N (%) | 49/108 (45.4)*** | 53/108 (49.1)*** | 4/109 (3.7) |
| SF-36 PCS score, LS mean change from baseline (SE)† | 5.91 (0.525)*** | 5.41 (0.524)*** | 1.82 (0.715) |
| HAQ-DI score, mean change from baseline (SE)† | −0.40 (0.036)*** | −0.41 (0.036)*** | −0.17 (0.047) |

TABLE 4-continued

Comparison of Efficacy at Week 24 (Placebo-controlled Phase) Across Several Arthritis, Psoriasis and Patient-reported Outcomes.

| Efficacy endpoint | Secukinumab 10 mg/kg i.v. → 150 mg s.c. | Secukinumab 10 mg/kg i.v. → 75 mg s.c. | Placebo |
|---|---|---|---|
| Biologic-naive subjects[a] | | | |
| ACR 20 response, n/N (%) | 78/143 (54.5)*** | 79/142 (55.6)*** | 25/143 (17.5) |
| ACR 50 response, n/N (%) | 57/143 (39.9)*** | 52/142 (36.6)*** | 12/143 (8.4) |
| ACR 70 response, n/N (%) | 32/143 (22.4)*** | 27/142 (19.0)*** | 4/143 (2.8) |
| Biologic-experienced subjects | | | |
| ACR 20 response, n/N (%) | 23/59 (39.0)** | 23/60 (38.3)** | 10/59 (16.9) |
| ACR 50 response, n/N (%) | 13/59 (22.0)* | 10/60 (16.7)* | 3/59 (5.1) |
| ACR 70 response, n/N (%) | 6/59 (10.2)* | 7/60 (11.7)* | 0/59 (0) |

*P < 0.05 versus placebo;
**P < 0.01 versus placebo;
***P < 0.001 versus placebo
[†]N = 202 in each group;
[‡]N = 185 in the secukinumab 10 mg/kg i.v. → 150 mg s.c. group, N = 181 in the secukinumab 10 mg/kg i.v. → 75 mg s.c. group and N = 179 in the placebo group. Minimal clinically important differences were ≥2.5 for SF-36 physical component score, and −0.35 for HAQ-DI score. Due to the lack of biologic-experienced subjects achieving an ACR 70 or PASI 90 response with placebo, a Fisher exact test was performed for between-treatment statistical analysis for the end points.
[a]Note, one subject received one dose of infliximab which was subsequently discontinued for logistical reasons, rather than due to inadequate response. This subject was reported as biologic-naïve.
ACR 20/50/70, 20%/50%/70% improvement in American College of Rheumatology response criteria; Biologic-experienced, documented inadequate response or lack of safety/tolerability with TNF inhibitor(s);
DAS28-CRP, 28-joint Disease Activity Score 28 based on C-reactive protein;
HAQ-DI, health assessment questionnaire disability index;
LS, least square;
MCID, minimum clinically important difference;
mTSS, modified total sharp score;
PASI 75/90, 75%/90% improvement in psoriasis area-and-severity index;
SE, standard error; SF-36
PCS, short form 36 physical component summary;
TNF, tumor necrosis factor.

Subjects in both secukinumab treatment groups experienced significantly less radiographic progression, as measured by change from baseline in mTSS, at Week 24 compared with placebo-treated subjects. Improvements were maintained through 52-weeks (FIG. 3).

Figure 4:
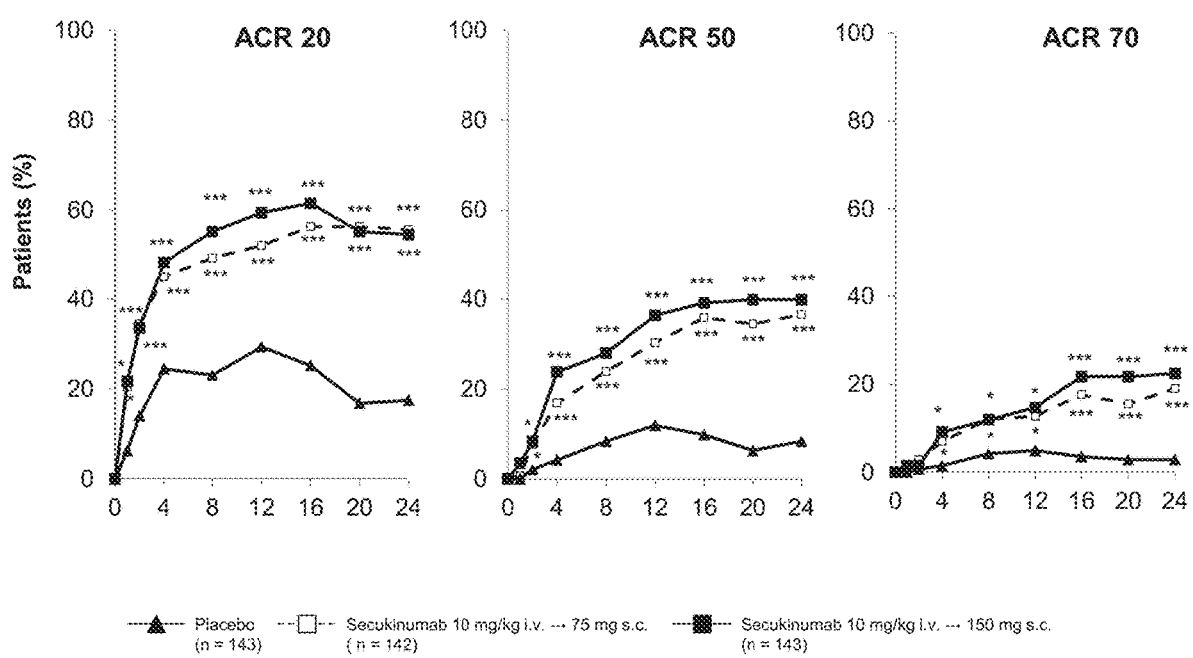
FIG. 4A-B. ACR responses through Week 24 in biologic-naïve and biologic-experienced subjects (non-responder imputation analysis). The proportion of subjects with a 20%, 50% and 70% improvement in ACR response criteria (ACR 20, ACR 50 and ACR 70, respectively) over time is shown for a) biologic-naïve subjects (FIG. 4A) and biologic-experienced (FIG. 4B) subjects. Missing data were imputed as nonresponses. *P<0.05, P<0.01, *P<0.001 versus placebo. No statistical comparison with placebo was possible for ACR 70 response at Week 24 in subjects who were biologic-experienced due to the absence of responders in the placebo group.
Figure 4B:
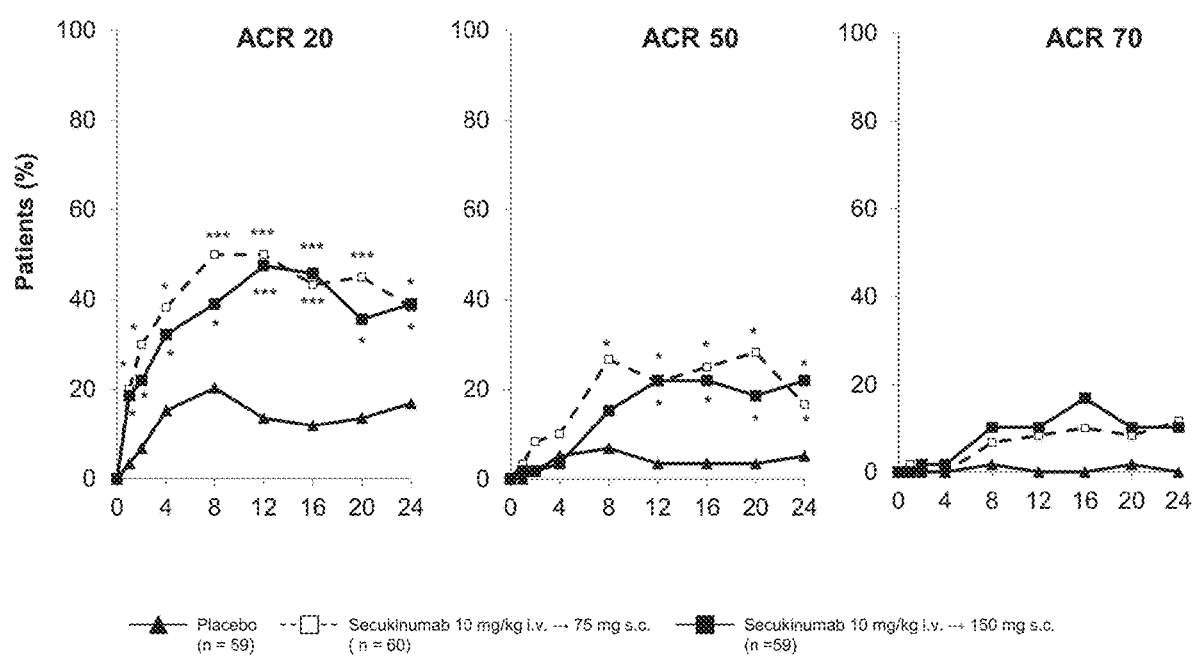
Figure 5:
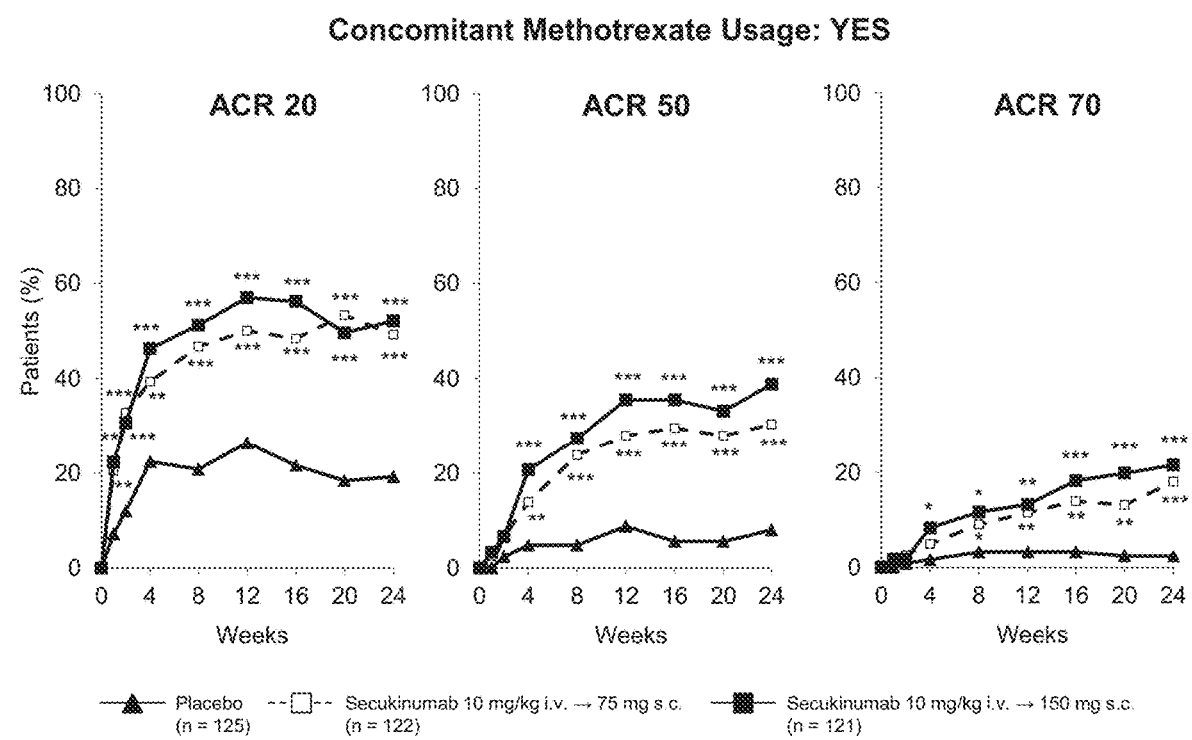
FIG. 5A-B. ACR responses over time to Week 24 in subjects with and without concomitant MTX (non-responder imputation analysis). The proportion of subjects with a 20%, 50% and 70% improvement in ACR response criteria (ACR 20, ACR 50 and ACR 70, respectively) over time to Week 24 is shown for subjects receiving concomitant methotrexate treatment (FIG. 5A), and subjects who did not receive concomitant MTX (FIG. 5B). Missing data were imputed as nonresponses. *P<0.05, P<0.01, *P<0.001 versus placebo.
Figure 5B:
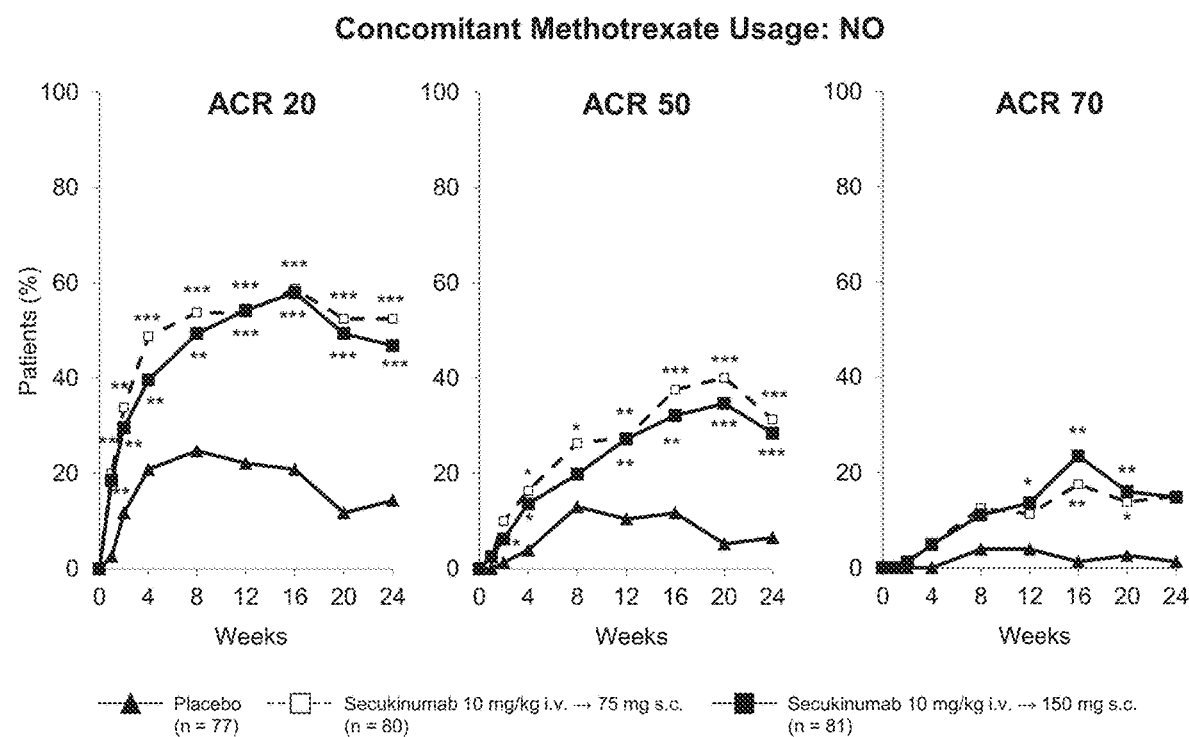

Improvements at Week 24 with secukinumab versus placebo were observed regardless of prior exposure to biologics. ACR response rates were higher with both doses of secukinumab versus placebo in both biologic-naïve and biologic-experienced subjects, although the magnitude of response was higher in biologic-naïve subjects (FIG. 4). Significant improvements in ACR response with secukinumab versus placebo were observed with and without concomitant methotrexate use, with similar responses observed in both populations (FIG. 5).

Clinical benefits with secukinumab treatment were maintained through 52 weeks of therapy (Table 5). At Week 52, ACR 20, ACR 50 and ACR 70 response rates, using an observed analysis, were 69.5%, 50.0% and 28.2% for secukinumab 10 mg/kg i.v. →150 mg s.c. and 66.9%, 38.4% and 25.6% for secukinumab 10 mg/kg i.v. →75 mg s.c., respectively (Table 5).

TABLE 5

Summary of Observed Efficacy Data at Week 52 Among Subjects Randomized to Secukinumab at Baseline.

| Efficacy endpoint | Secukinumab 10 mg/kg i.v. → 150 mg s.c. | Secukinumab 10 mg/kg i.v. → 75 mg s.c. |
|---|---|---|
| ACR 20 response, n/N (%) | 121/174 (69.5) | 115/172 (66.9) |
| ACR 50 response, n/N (%) | 87/174 (50.0) | 66/172 (38.4) |
| ACR 70 response, n/N (%) | 49/174 (28.2) | 44/172 (25.6) |
| DAS28-CRP, LS mean change from baseline (SE) | −1.82 (1.162) | −1.90 (1.223) |
| Subjects with dactylitis, n/N (%) | 22/179 (12.3) | 18/175 (10.3) |
| Subjects with enthesitis, n/N (%) | 33/179 (18.4) | 36/175 (20.6) |
| PASI 75 response, n/N (%) | 83/99 (83.8) | 71/99 (71.7) |
| PASI 90 response, n/N (%) | 64/99 (64.6) | 52/99 (52.5) |
| SF-36 PCS score, LS mean change from baseline (SE) | 6.79 (7.455) | 5.56 (7.432) |
| HAQ-DI score, mean change from baseline (SE) | −0.46 (0.512) | −0.45 (0.606) |

ACR 20/50/70, 20%/50%/70% improvement in American College of Rheumatology response criteria;
DAS28-CRP, 28-joint Disease Activity Score 28 based on C-reactive protein;
HAQ-DI, health assessment questionnaire disability index;
LS, least square;
PASI 75/90, 75%/90% improvement in psoriasis area-and-severity index;
SE, standard error;
SF-36 PCS, short form 36 physical component summary Example 3

PsA Trial A1N457F2306 (FUTURE 1) Radiographic Results Week 24 and 52 Summary 606 adults with moderate to severe PsA were randomized to placebo (PBO) or one of two secukinumab treatment arms: secukinumab 10 mg/kg i.v. followed by 75 mg s.c. (10 IV→75 SC) or 150 mg s.c. (10 IV→150 SC). All patients were assessed for joint response at Week 16 (based on ≥20% improvement in tender and swollen joint counts). PBO-treated patients were re-randomized to secukinumab 75 or 150 mg s.c. at Week 16 (non-responders) or Week 24 (responders). The van der Heijde total modified Sharp scores (vdH-mTSS, mTSS), and erosion and joint space narrowing (JSN) scores were determined at baseline, Weeks 16/24 (depending on response) and 52. The effect of secukinumab on radiographic progression from baseline to Week 24 was evaluated using a non-parametric ANCOVA model, with linear extrapolation for patients who had x-ray assessments at Week 16. Exploratory analyses assessed the proportion of patients with no structural progression (defined as change from baseline in mTSS ≤0.5) and maintenance of this effect over time. The changes from baseline in mTSS, erosion and JSN scores demonstrated that secukinumab-treated patients had statistically significantly less progression from baseline to Week 24 compared with PBO-treated patients, regardless of whether patients had received prior therapy with a TNF inhibitor, were on secukinumab monotherapy, or were receiving concomitant methotrexate (MTX; Table 6). Inhibition of joint structural damage was sustained with secukinumab through Week 52. Analysis of PBO patients who switched to secukinumab showed a greater mean change from baseline in mTSS for the PBO group from baseline to Week 24 (mean increase of 0.48) vs. the period from Week 24 to Week 52 when patients had been switched to secukinumab (mean decrease of −0.03), providing additional support for efficacy. Analyses of patients who had x-rays at both Week 16/24 and Week 52 (X-ray completers) showed that the proportion of patients who experienced no progression (using a threshold of ≤0.5 in X-ray completers) from randomization to Week 24 vs. the period from Week 24 to Week 52 was consistently high in the secukinumab groups: 92.3% vs. 85.8%, respectively, for 10 IV→75 SC and 82.3% vs. 85.7% for 10 IV→150 SC. In patients initially randomized to PBO, 75.7% had no progression from randomization to Week 24 and this increased to 86.8% for the period from Week 24 to Week 52 following active treatment with secukinumab (P <0.05). The threshold of ≤0.5 is, within the margin of error of reading, considered clinically meaningful for PsA and is used by other studies of biologics in PsA to quantify inhibition of radiographic progression (Mease et al. (2009)).

TABLE 6

Radiographic progression at Week 24 by treatment group

| Week 24 (Mean change from baseline) | Secukinumab 10 mg/kg IV → 75 mg SC n = 202 | Secukinumab 10 mg/kg IV → 150 mg SC n = 202 | Placebo n = 202 |
|---|---|---|---|
| mTSS | 0.02† | 0.13† | 0.57 |
| Erosion score | 0.08† | 0.04‡ | 0.35 |
| JSN score | −0.06† | 0.10 | 0.23 |
| TNF-naïve/IR | n = 142/n = 60 | n = 143/n = 59 | n = 143/n = 59 |
| mTSS | −0.06†/0.21 | 0.15/0.10† | 0.57/0.58 |
| Erosion score | 0/0.25 | 0.02/0.08‡ | 0.29/0.50 |
| JSN score | −0.06†/−0.05 | 0.13/0.02 | 0.28/0.09 |
| Concomitant MTX use, yes/no | n = 122/n = 80 | n = 121/n = 81 | n = 125/n = 77 |

TABLE 6-continued

Radiographic progression at Week 24 by treatment group

| Week 24 (Mean change from baseline) | Secukinumab 10 mg/kg IV → 75 mg SC n = 202 | Secukinumab 10 mg/kg IV → 150 mg SC n = 202 | Placebo n = 202 |
|---|---|---|---|
| mTSS | −0.07†/0.14 | 0.14/0.12 | 0.57/0.58 |
| Erosion score | 0.01†/0.17 | 0.04†/0.02 | 0.34/0.37 |
| JSN score | −0.08/−0.03 | 0.10/0.10 | 0.24/0.21 |

†P < 0.05 vs. placebo;
‡P < 0.01 vs. placebo
JSN, joint space narrowing;
mTSS, modified total Sharp score;
MTX, methotrexate;
TNF-naïve/IR, tumor necrosis factor inhibitor naïve/inadequate responder
P-values based on a non-parametric ANCOVA model.

These results demonstrate that radiographic benefits with secukinumab were observed up to Week 24, regardless of prior anti-TNF exposure. From Week 24 to Week 52, sustained inhibition of radiographic progression was observed with secukinumab in the TNF-alpha inhibitor naïve subgroup to a greater extent than in those patients who were TNF-alpha inhibitor inadequate responders.

Example 4

Additional Analysis of Inhibition of Structural Damage by Secukinumab in PsA Patients (FUTURE 1)

Figure 6:
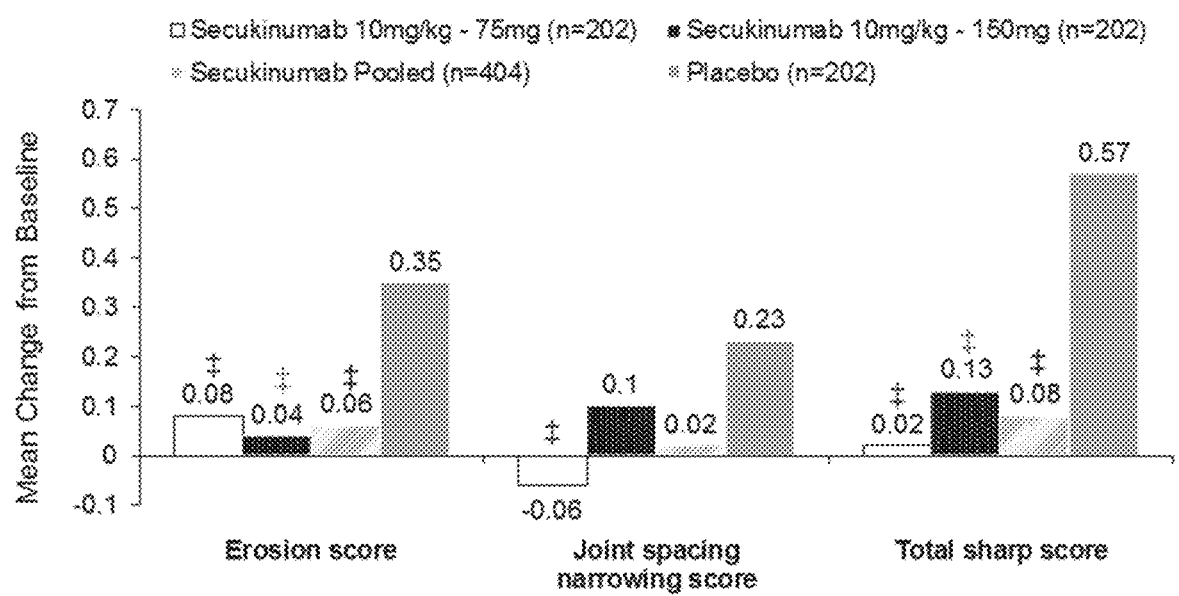
FIG. 6. Secukinumab 75 mg and 150 mg is superior to placebo in inhibiting progression of joint structural damage measured by vdH-mTSS at Week 24. Entire Population (FAS). P ≤0.05 vs. placebo. Missing values at Week 24 were imputed by linear extrapolation.

Further analysis was performed in order to determine the effect of secukinumab on joint structural damage at Week 24 and Week 52. As shown in FIG. 6, there was a significant improvement with both secukinumab 75 mg & 150 mg dose vs placebo in erosion score, joint space narrowing score (75 mg) and van der Heijde modified total Sharp score (mTSS, vdH-mTSS) at Week 24 in the full analysis set (FAS).

Figure 7:
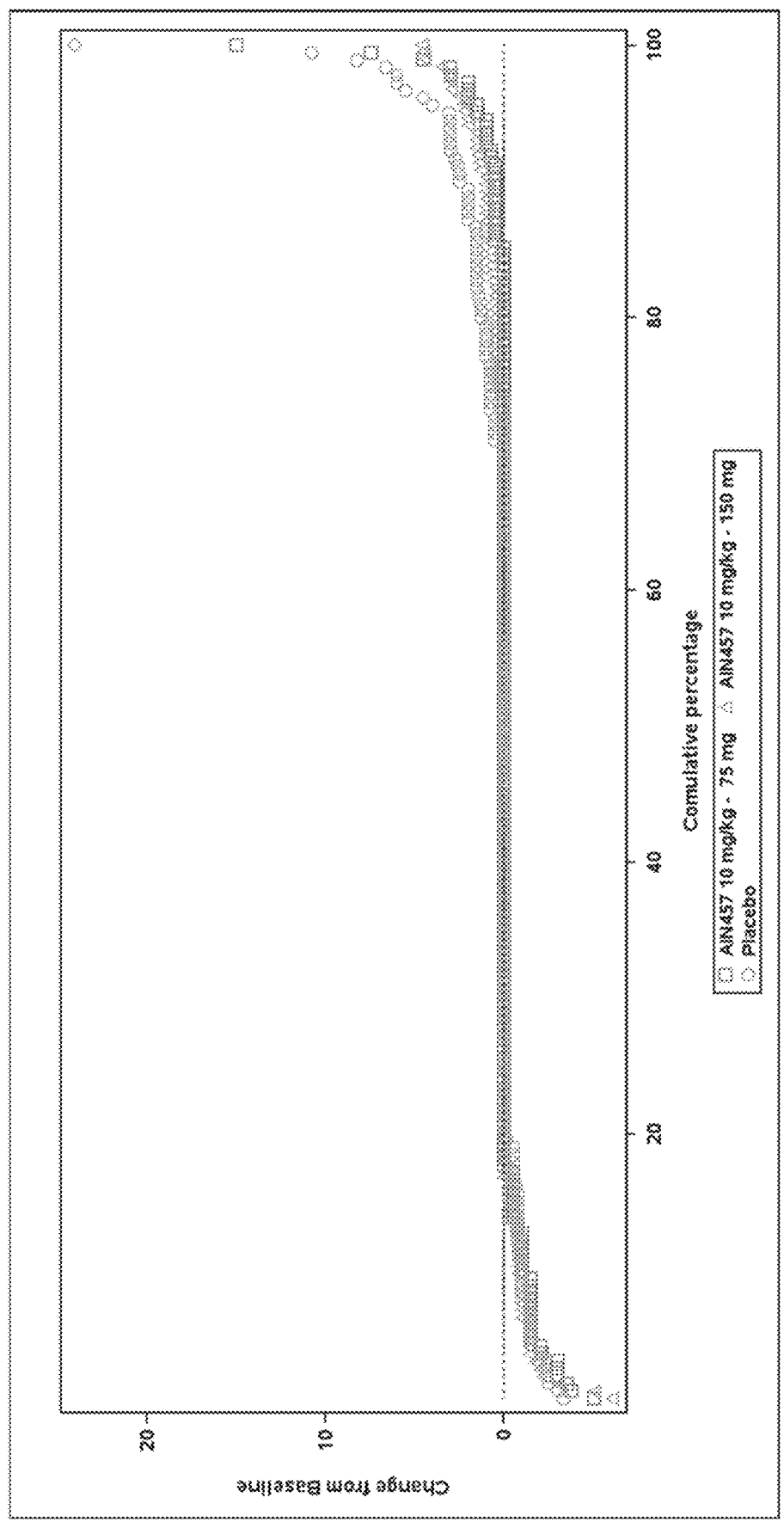
FIG. 7. Cumulative distribution plot for week 24 total vdH-mTSS score.

The Cumulative Distribution Plot (FIG. 7) for the total vdH-mTSS score, also called "S curve", shows individual patient data, indicating whether there are outliers driving the mean. The gray circles represent placebo patients and it can be seen that more of these patients had greater change from baseline (suggesting progression of structural damage), than either the 10 mg/kg −150 or −75 group. The two major outliers (one in placebo one in secukinumab) do not change the overall result, implying that the results are not driven by a few placebo patients having large progression during this time.

Figure 8:
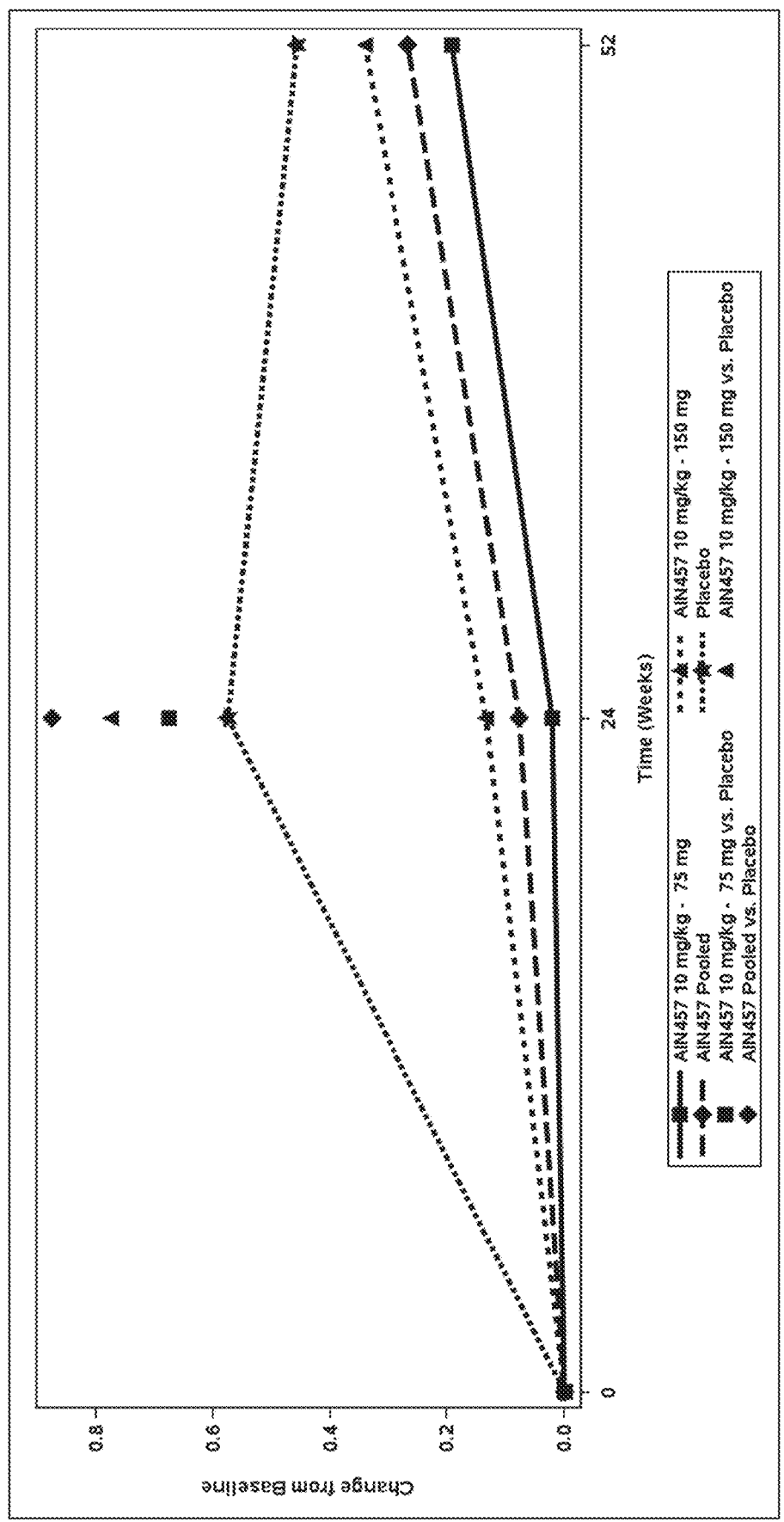
FIG. 8. Total vdH-mTSS progression over time.

As shown in FIG. 8, both the 10 mg/kg→150 mg and →75 mg group displayed reduced total vdH-mTSS progression compared to placebo over time. Note, by week 24, all placebo patients were switched to secukinumab at 75 or 150 mg s.c. The change from baseline in these placebo-switched patients begins to decrease at Week 24. This is also shown in Table 7. Thus, s.c. treatment with secukinumab (with or without a loading dose), appears to inhibit the progression of structural damage associated with PsA.

Figure 9:
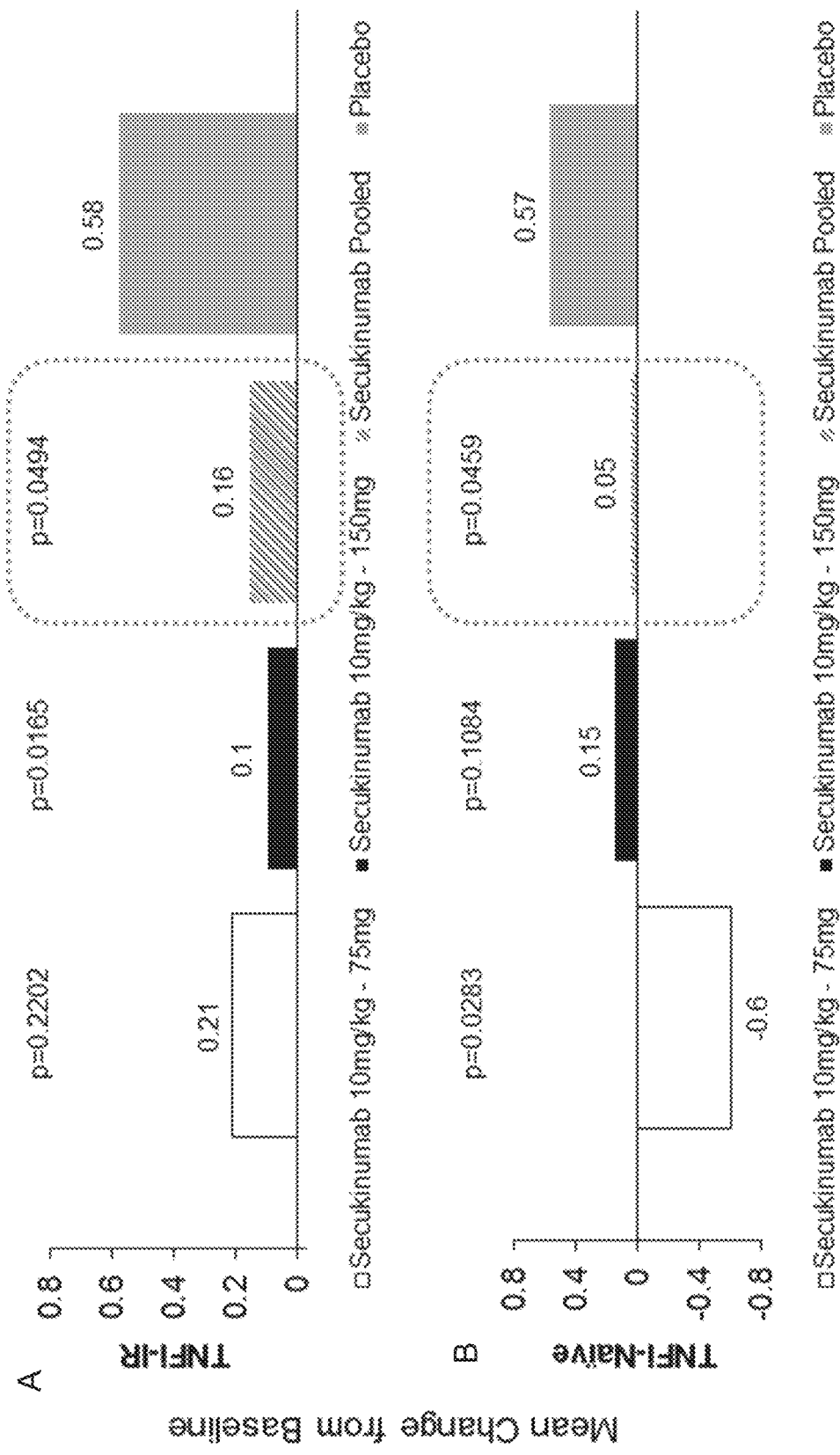
FIG. 9A-B. Secukinumab shows significant inhibition of structural damage in both TNF-Naïve (FIG. 9A) and TNF-Inadequate Responders (FIG. 9B) as measured by vdH-mTSS.

FIG. 9 provides an analysis of the inhibition of structural damage, as measured by vdH-mTSS in TNF-IR (FIG. 9A) and TNF-naïve (FIG. 9B) patients at Week 24. Both the 10 mg/kg→150 mg and →75 mg groups—separately or pooled-displayed reduced mean change from baseline compared to placebo over time. Notably, secukinumab shows significant inhibition of structural damage in both TNF-naïve and TNF-IR PsA patients (boxed). This is also shown in Table 8. To our knowledge, secukinumab is the first biological to exhibit inhibition of progression of structural damage in PsA patients who have been previously treated with a TNF alpha antagonist (e.g., TNF-IR patients). Secukinumab also shows significant inhibition of structural damage in patients regardless of concomitant MTX treatment (Table 9).

Figure 10:
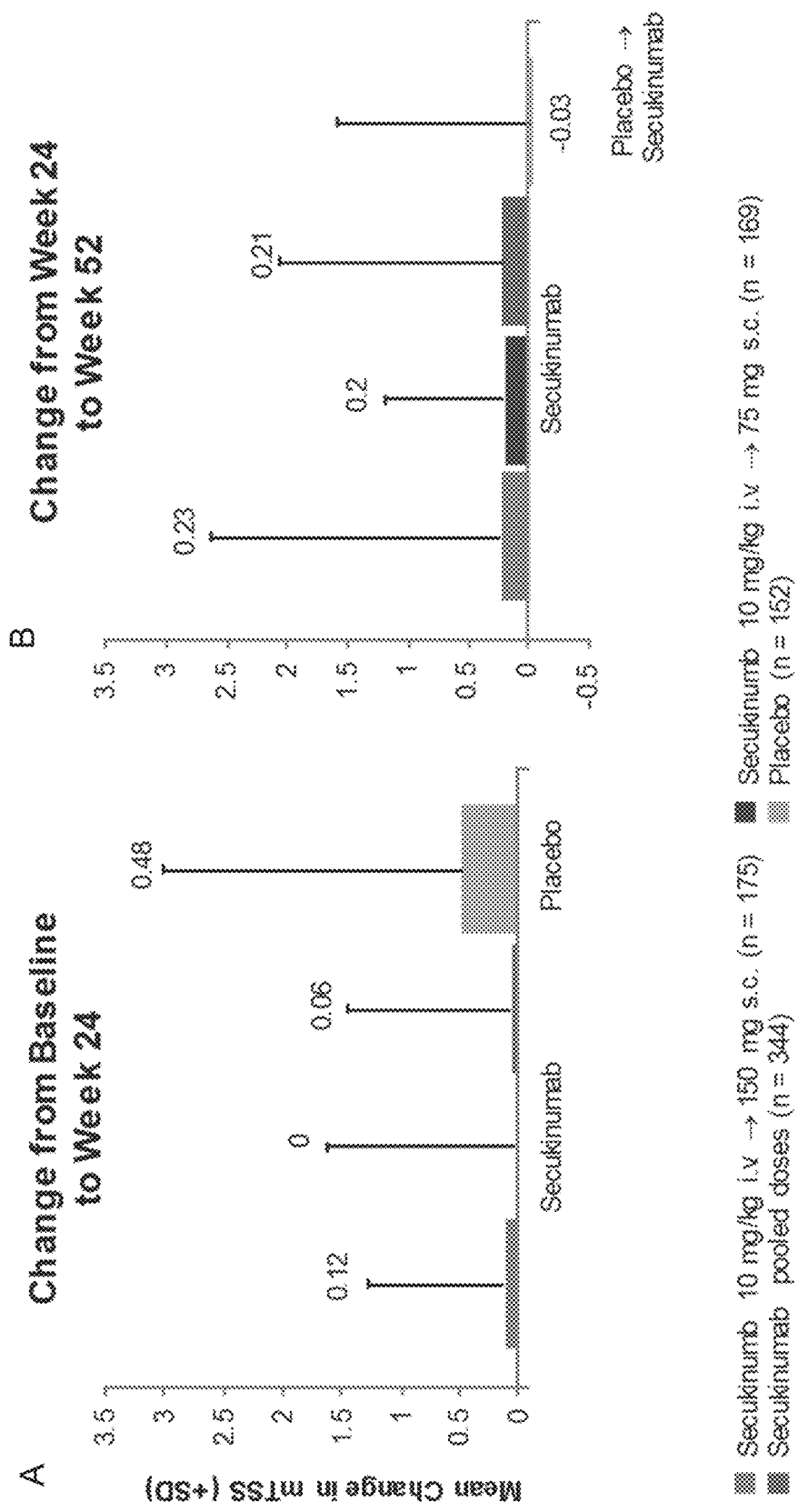
FIG. 10A-B. Mean (+standard deviation) changes in mTSS for X-ray completers (i.e., patients who had X-ray measures at baseline, Week 16/24 and Week 52) during two time periods, baseline to week 24 (FIG. 10A) and week 24 to week 52 (FIG. 10B). IV, intravenous; mTSS, modified total Sharp score; SC, subcutaneous; SD, standard deviation
Figure 11:
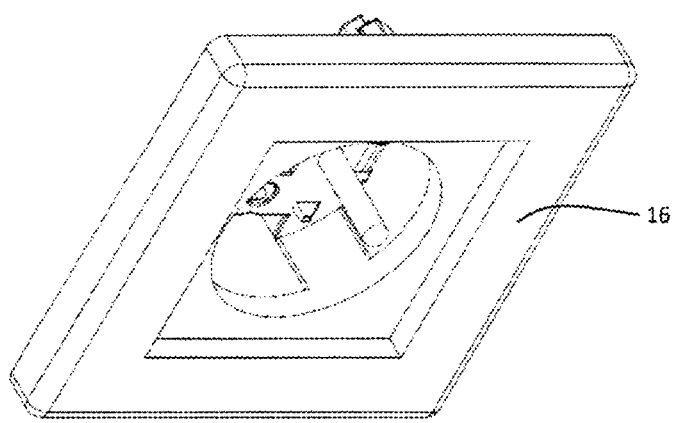
Figure 12:
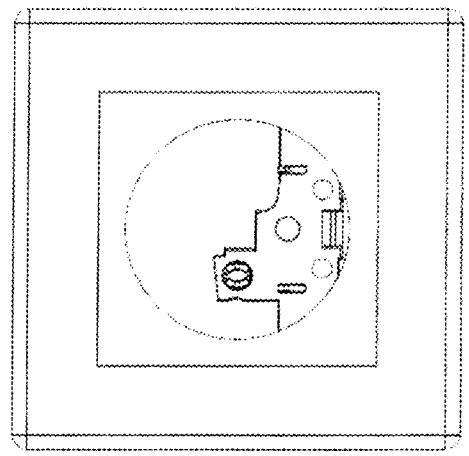
Figure 13:
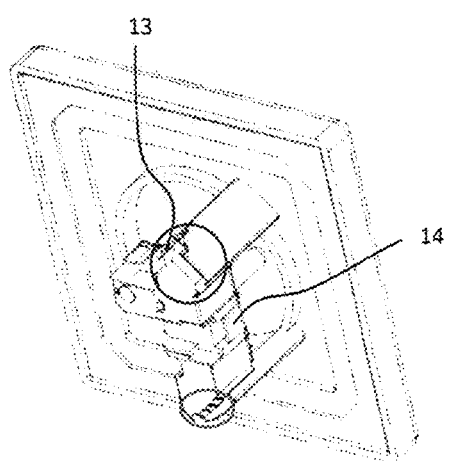
Figure 14:
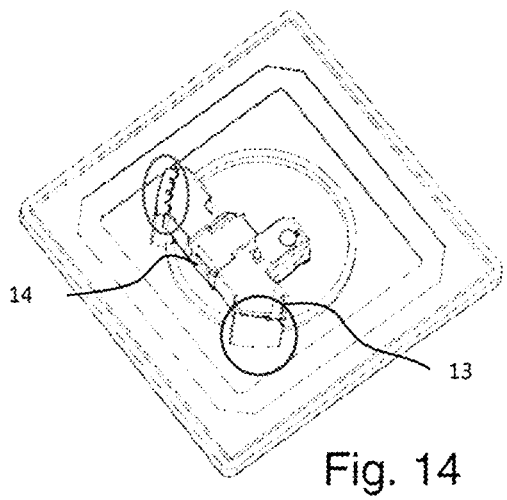
Figure 15:
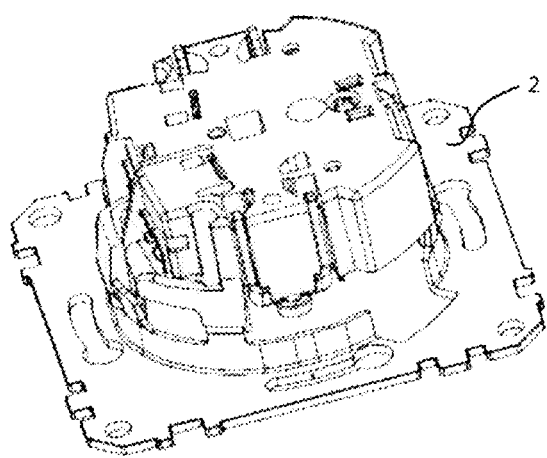
Figure 16:
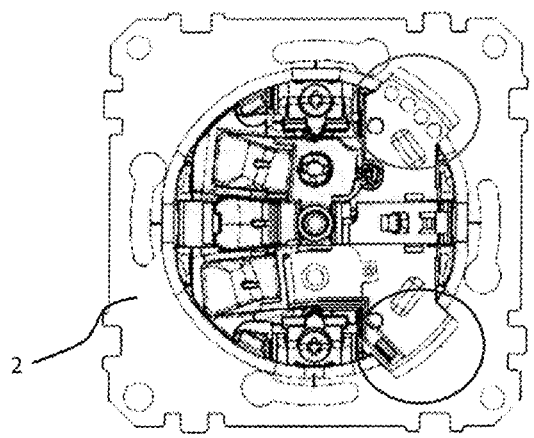
Figure 17:
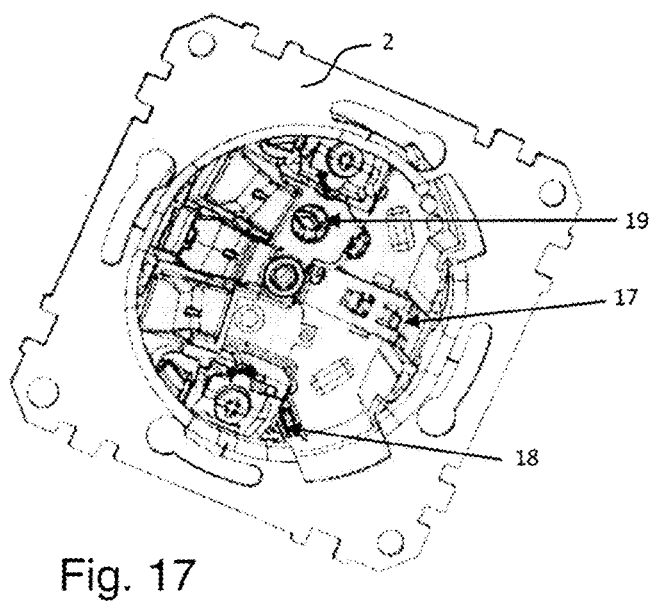

X-ray completers were defined as patients who had X-ray assessments at baseline, Week 16 or 24 and Week 52. The number of x-ray completers was 175 (86.6%) for the 10 IV→150 SC group, 169 (83.7%) for the 10 IV→75 SC group and 152 (75.3%) for the placebo group. The number of patients who had linear extrapolation applied to the Week 24 endpoint was 55 in the secukinumab 10 IV→150 SC group, 40 in the secukinumab 10 IV→75 SC group and 109 in the placebo group. Data from the X-ray completers demonstrated a sustained therapeutic effect with secukinumab for up to 1 year (FIG. 10). The mean change in mTSS between Weeks 24 (including linear extrapolation for non-responders) and 52 (FIG. 10B) for the placebo patients who switched to secukinumab was −0.03 compared with 0.48 for the placebo period (baseline to Week 24 [FIG. 10A]), indicating an inhibition of radiographic disease progression with secukinumab (FIG. 10).

Data from X-ray completers showed that a high proportion of secukinumab patients experienced no progression from randomization to Week 24 and from Week 24 to Week 52. In the 10 IV→150 SC secukinumab group, 82.3% of patients showed no progression from randomization to Week 24 and 85.7% of patients showed no progression from Week 24 to Week 52. The proportions of patients showing no progression in the 10 IV→75 SC secukinumab group were 92.3% and 85.8%, respectively. The proportion of placebo-treated patients with no structural progression significantly increased from 75.7% (randomization to Week 24) to 86.8% (Week 24 to Week 52) following secukinumab treatment (P<0.05).

The 1-year results of the FUTURE 1 trial reported here demonstrate that anti-IL-17A therapy with secukinumab inhibits radiographic disease progression in patients with PsA. The radiographic benefits of treatment seen at 24 weeks were sustained for up to 1 year and were observed irrespective of prior anti-TNF treatment. Improvements were also noted in patients receiving concomitant methotrexate therapy as well as patients who were methotrexate-naive. Progression of joint structural damage in placebo-treated patients was inhibited by switching to secukinumab treatment, indicating that delayed treatment was still beneficial and that a loading regimen of secukinumab is not necessarily required to achieve this result. Furthermore, exploratory analyses showed that a high proportion of secukinumab-treated patients experienced no structural progression.

A recent systematic review highlighted the inhibitory effect of TNF blockers on structural damage in PsA (Goulabchand et al (2014) Ann Rheum Dis 73:414-9). However, failure of anti-TNF treatment, loss of efficacy and intolerance in some patients means that there is an urgent unmet need for therapies with an alternative mechanism of action (Mease et al (2014) Drugs 74:423-41; Saad et al (2009) Arthritis Res Ther 11: R52; Fagerli et al (2013) Ann Rheum Dis 72:1840-4). To this end, the results from the present study indicate that selective inhibition of IL-17A is beneficial to patients with PsA and may offer an additional therapeutic opportunity.

TABLE 7

Total sharp score (mTSS) Change from Week 24 to Week 52 in F2306 study for x-ray completers. Change from W24 = change from baseline to week 52 with evaluable cases minus change from baseline to Week 24 with linear extrapolation.

| Statistics | IV-75 mg (N = 169) | | IV-150 mg (N = 175) | | AIN pooled (N = 344) | | Placebo (N = 152) | |
| --- | --- | --- | --- | --- | --- | --- | --- | --- |
| | Change from BL | Change from W24 | Change from BL | Change from W24 | Change from BL | Change from W24 | Change from BL | Change from W24 |
| n | 169 | 169 | 175 | 175 | 344 | 344 | 152 | 152 |
| Mean | 0.00 | 0.20 | 0.12 | 0.23 | 0.06 | 0.21 | 0.48 | −0.03 |
| (SD) | (1.627) | (1.001) | (1.151) | (2.412) | (1.404) | (1.855) | (2.528) | (1.615) |
| Min | −5.0 | −3.0 | −6.0 | −3.0 | −6.0 | −3.0 | −3.3 | −11.8 |
| Median | 0.00 | 0.00 | 0.00 | 0.00 | 0.00 | 0.00 | 0.00 | 0.00 |
| Max | 15.0 | 7.0 | 4.6 | 28.5 | 15.0 | 28.5 | 24.0 | 6.0 |

TABLE 8

Total sharp score (mTSS) at week 24 by TNF alpha status.

| Concomitant Use | Treatment group | n | Mean change | Estimate (vs placebo) | P-values |
| --- | --- | --- | --- | --- | --- |
| TNF-IR | IV-75 mg (N = 60) | 53 | 0.21 | −0.35 | 0.2202 |
| | IV-150 mg (N = 59) | 50 | 0.10 | −0.64 | 0.0165 |
| | AIN457 Pooled (N = 119) | 103 | 0.16 | −0.47 | 0.0494 |
| | Placebo (N = 59) | 50 | 0.58 | | |
| TNF naive | IV-75 mg (N = 142) | 128 | −0.06 | −0.62 | 0.0283 |
| | IV-150 mg (N = 143) | 135 | 0.15 | −0.42 | 0.1084 |
| | AIN457 Pooled (N = 285) | 263 | 0.05 | −0.51 | 0.0459 |
| | Placebo (N = 143) | 129 | 0.57 | | |

TABLE 9

Total sharp score (mTSS) at Week 24 by concomitant MTX

| Concomitant Use | Treatment group | n | Mean change | Estimate | P-values |
| --- | --- | --- | --- | --- | --- |
| MTX = Yes | IV-75 mg (N = 122) | 105 | −0.07 | −0.58 | 0.0210 |
| | IV-150 mg (N = 121) | 111 | 0.14 | −0.39 | 0.0749 |
| | AIN457 Pooled (N = 243) | 216 | 0.04 | −0.47 | 0.0113 |
| | Placebo (N = 125) | 114 | 0.57 | | |

TABLE 9-continued

Total sharp score (mTSS) at Week 24 by concomitant MTX

| Concomitant Use | Treatment group | n | Mean change | Estimate | P-values |
|---|---|---|---|---|---|
| MTX = No | IV-75 mg (N = 80) | 76 | 0.14 | −0.44 | 0.2955 |
| | IV-150 mg (N = 81) | 74 | 0.12 | −0.58 | 0.1540 |
| | AIN457 Pooled (N = 161) | 150 | 0.13 | −0.53 | 0.1916 |
| | Placebo (N = 77) | 65 | 0.58 | | |

Example 5

Clinical Trial CAIN457F2312 (FUTURE 2):
Secukinumab Improves Active PsA in a Phase 3
Randomized, Multicenter, Double-Blind,
Placebo-Controlled Study Using a Subcutaneous
Dosing Regimen: Week 24 Results The objective was to evaluate the efficacy and safety of s.c. loading and maintenance dosing with secukinumab in FUTURE 2 (NCT01752634), a randomized, double-blind, placebo (PBO)-controlled phase 3 study in patients with active PsA.

397 adults with active PsA were randomized to s.c. secukinumab (300, 150 or 75 mg) or PBO at baseline (Week 0), Week 1, 2, 3, 4 and then every 4 weeks thereafter. Randomization was stratified by prior exposure to anti-TNF therapy. The primary endpoint was ACR20 response at Week 24. Secondary endpoints included PASI 75/90, Disease Activity Score 28 using C-reactive protein (DAS28-CRP), Short Form-36 Physical Component Summary (SF-36 PCS), Health Assessment Questionnaire-Disability Index (HAQ-DI), ACR50, dactylitis and enthesitis. Primary and secondary endpoints were included in a hierarchical testing analysis to adjust for multiplicity.

At Week 24, ACR20 responses were significantly greater with secukinumab 300, 150 and 75 mg than PBO: 54.0%, 51.0% and 29.3% vs. 15.3%, respectively (P<0.0001 for secukinumab 300 and 150 mg; P<0.05 for 75 mg vs PBO). Secukinumab 300 and 150 mg also improved secondary endpoints, including significant improvements in PASI 75/90 scores and DAS-28 CRP vs. PBO (Table 10). Exposure-adjusted rates of treatment-emergent AEs (maximum exposure to secukinumab: 372 days) were 222.2 and 309.3 cases per 100 pt-years amongst secukinumab (pooled) and placebo-treated subjects, respectively. The respective rates of serious AEs were 7.8 and 8.8.

Secukinumab 300 and 150 mg s.c. demonstrated clinically significant improvements in the signs and symptoms of PsA. The safety profile of secukinumab was consistent with that previously reported.

TABLE 10

Summary of FUTURE 2 selected 24-week efficacy results

| Week 24 Data | Secukinumab 300 mg s.c. | Secukinumab 150 mg s.c. | Secukinumab 75 mg s.c. | PBO |
|---|---|---|---|---|
| ACR20 (% responders) | 54.0* | 51.0* | 29.3‡ | 15.3 |
| ACR50 (% responders) | 35.0§ | 35.0 | 18.2 | 7.1 |
| PASI 75 (% responders) | 63.4* | 48.3§ | 28.0 | 16.3 |
| PASI 90 (% responders) | 48.8† | 32.8§ | 12.0 | 9.3 |
| DAS28-CRP, LS mean change from baseline | −1.61§ | −1.58§ | −1.12 | −0.96 |
| aDactylitis (resolution of, %) | | 46.8 | | 14.8 |
| aEnthesitis (resolution of, %) | | 40.4 | | 21.5 |

*P < 0.0001;
†P < 0.001;
§P < 0.01;
‡P < 0.05 vs PBO;
P-values adjusted for multiplicity.
aData from patients with dactylitis (n = 138) and enthesitis (n = 253) at baseline.
LS, least squares.

What is claimed is:

1. A method of inhibiting the progression of structural damage in a patient having psoriatic arthritis (PsA), comprising selectively administering to the patient a dose of about 300 mg of an anti-Interleukin-17 (IL-17) antibody by subcutaneous injection every 4 weeks, wherein the patient is selected for treatment with the dose of about 300 mg based on the patient previously failing treatment with a Tumor Necrosis Factor (TNF) alpha antagonist or previously responding inadequately to treatment with a TNF alpha antagonist, and wherein:
   i) the anti-IL-17 antibody comprises an immunoglobulin $V_H$ domain comprising the amino acid sequence set forth as SEQ ID NO:8 and an immunoglobulin $V_L$ domain comprising the amino acid sequence set forth as SEQ ID NO:10;
   ii) the anti-IL-17 antibody comprises an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6;
   iii) the anti-IL-17 antibody comprises an immunoglobulin $V_H$ domain comprising the hypervariable regions set forth as SEQ ID NO:11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6;
   iv) the anti-IL-17 antibody comprises an immunoglobulin light chain comprising the amino acid sequence set forth as SEQ ID NO:14 and an immunoglobulin heavy chain comprising the amino acid sequence set forth as SEQ ID NO:15; or
   v) the anti-IL-17 antibody is secukinumab.

2. The method according to claim 1, wherein the anti-IL-17 antibody is administered concomitantly with a disease-modifying anti-rheumatic drug (DMARD) selected from the group consisting of hydroxychloroquine, chloroquine, sulfasalazine, leflunomide, azathioprine, cyclosporine, gold salts, minocycline, cyclophosphamide, D-penicillamine, minocycline, auranofin, tacrolimus, myocrisin, methotrexate, and chlorambucil.

3. The method according to claim 1, wherein the progression of erosion, joint space narrowing, pencil-in-cup phenomena, joint widening, joint narrowing, subluxation, bony proliferation, osteolysis, or ankylosis is inhibited in the patient.

4. The method according to claim 1, wherein following administration of the anti-IL-17 antibody, the patient experiences:
   a) a change from baseline in the van der Heijde psoriatic arthritis-modified total Sharp score (mTSS) of ≤0.5;
   b) a change from baseline in erosion score of ≤0.3; and/or
   c) a change from baseline in joint space narrowing (JSN) score of ≤0.2.

5. The method according to claim 1, wherein the anti-IL-17 antibody is secukinumab.

6. The method according to claim 5, wherein secukinumab is disposed in a liquid pharmaceutical composition that is not reconstituted from a lyophilisate.

7. The method according to claim 6, wherein the concentration of secukinumab in the liquid pharmaceutical composition is 150 mg/ml.

8. The method according to claim 7, wherein 1 or 2 milliliters of the liquid pharmaceutical composition is disposed within an injection pen, a pre-filled syringe, or an autoinjector.

9. The method according to claim 6, wherein the liquid pharmaceutical composition further comprises a buffer, carrier, diluent, filler, salt, stabilizer, or solubilizer.

10. The method according to claim 1, wherein the anti-IL-17 antibody is administered concomitantly with a non-steroidal anti-inflammatory drug (NSAID) selected from the group consisting of a propionic acid derivative, acetic acid derivative, enolic acid derivative, fenamic acid derivative, Cox inhibitor, lumiracoxib, ibuprofen, fenoprofen, ketoprofen, flurbiprofen, oxaprozin, indomethacin, sulindac, etodolac, ketorolac, nabumetone, aspirin, naproxen, valdecoxib, etoricoxib, rofecoxib, acetominophen, celecoxib, diclofenac, tramadol, piroxicam, meloxicam, tenoxicam, droxicam, lornoxicam, isoxicam, mefanamic acid, meclofenamic acid, flufenamic acid, tolfenamic, valdecoxib, parecoxib, etodolac, indomethacin, aspirin, ibuprofen, and firocoxib.

11. The method according to claim 1, wherein the anti-IL-17 antibody is administered concomitantly with a steroid selected from the group consisting of prednisolone, prednisone, dexamethasone, cortisol, cortisone, hydrocortisone, methylprednisolone, betamethasone, triamcinolone, beclometasome, fludrocortisone, deoxycorticosterone, and aldosterone.

12. A method of inhibiting the progression of structural damage in a patient having psoriatic arthritis (PsA), comprising selectively administering to the patient a dose of about 300 mg of an anti-Interleukin-17 (IL-17) antibody by subcutaneous injection with dosing at week 0, 1, 2, 3, and 4, followed by dosing every 4 weeks, wherein the patient is selected for treatment with the dose of about 300 mg based on the patient previously failing treatment with a Tumor Necrosis Factor (TNF) alpha antagonist or previously responding inadequately to treatment with a TNF alpha antagonist, and wherein:
   i) the anti-IL-17 antibody comprises an immunoglobulin $V_H$ domain comprising the amino acid sequence set forth as SEQ ID NO:8 and an immunoglobulin $V_L$ domain comprising the amino acid sequence set forth as SEQ ID NO:10;
   ii) the anti-IL-17 antibody comprises an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6;
   iii) the anti-IL-17 antibody comprises an immunoglobulin $V_H$ domain comprising the hypervariable regions set forth as SEQ ID NO:11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6;
iv) the anti-IL-17 antibody comprises an immunoglobulin light chain comprising the amino acid sequence set forth as SEQ ID NO:14 and an immunoglobulin heavy chain comprising the amino acid sequence set forth as SEQ ID NO:15; or
v) the anti-IL-17 antibody is secukinumab.

13. The method according to claim 12, wherein the anti-IL-17 antibody is administered concomitantly with a disease-modifying anti-rheumatic drug (DMARD) selected from the group consisting of hydroxychloroquine, chloroquine, sulfasalazine, leflunomide, azathioprine, cyclosporine, gold salts, minocycline, cyclophosphamide, D-penicillamine, minocycline, auranofin, tacrolimus, myocrisin, methotrexate, and chlorambucil.

14. The method according to claim 12, wherein the progression of erosion, joint space narrowing, pencil-in-cup phenomena, joint widening, joint narrowing, subluxation, bony proliferation, osteolysis, or ankylosis is inhibited in the patient.

15. The method according to claim 12, wherein following administration of the anti-IL-17 antibody, the patient experiences:
   a) a change from baseline in the van der Heijde psoriatic arthritis-modified total Sharp score (mTSS) of ≤0.5;
   b) a change from baseline in erosion score of ≤0.3; and/or
   c) a change from baseline in joint space narrowing (JSN) score of ≤0.2.

16. The method according to claim 12, wherein the anti-IL-17 antibody is secukinumab.

17. The method according to claim 16, wherein secukinumab is disposed in a liquid pharmaceutical composition that is not reconstituted from a lyophilisate.

18. The method according to claim 17, wherein the concentration of secukinumab in the liquid pharmaceutical composition is 150 mg/ml.

19. The method according to claim 18, wherein 1 or 2 milliliters of the liquid pharmaceutical composition is disposed within an injection pen, a pre-filled syringe, or an autoinjector.

20. The method according to claim 17, wherein the liquid pharmaceutical composition further comprises a buffer, carrier, diluent, filler, salt, stabilizer, or solubilizer.

21. The method according to claim 12, wherein the anti-IL-17 antibody is administered concomitantly with a non-steroidal anti-inflammatory drug (NSAID) selected from the group consisting of a propionic acid derivative, acetic acid derivative, enolic acid derivative, fenamic acid derivative, Cox inhibitor, lumiracoxib, ibuprophen, fenoprofen, ketoprofen, flurbiprofen, oxaprozin, indomethacin, sulindac, etodolac, ketorolac, nabumetone, aspirin, naproxen, valdecoxib, etoricoxib, rofecoxib, acetominophen, celecoxib, diclofenac, tramadol, piroxicam, meloxicam, tenoxicam, droxicam, lornoxicam, isoxicam, mefanamic acid, meclofenamic acid, flufenamic acid, tolfenamic, valdecoxib, parecoxib, etodolac, indomethacin, aspirin, ibuprophen, and firocoxib.

22. The method according to claim 12, wherein the anti-IL-17 antibody is administered concomitantly with a steroid selected from the group consisting of prednisolone, prednisone, dexamethasone, cortisol, cortisone, hydrocortisone, methylprednisolone, betamethasone, triamcinolone, beclometasome, fludrocortisone, deoxycorticosterone, and aldosterone.

* * * * *

SEQUENCE LISTING

```
<160> NUMBER OF SEQ ID NOS: 15

<210> SEQ ID NO 1
<211> LENGTH: 5
<212> TYPE: PRT
<213> ORGANISM: artificial
<220> FEATURE:
<223> OTHER INFORMATION: CDR1 = hypervariable region 1 of heavy chain of
      AIN457

<400> SEQUENCE: 1

Asn Tyr Trp Met Asn
1               5

<210> SEQ ID NO 2
<211> LENGTH: 17
<212> TYPE: PRT
<213> ORGANISM: ARTIFICIAL
<220> FEATURE:
```

```
<223> OTHER INFORMATION: CDR2 = hypervariable region 2 of heavy chain of
      AIN457

<400> SEQUENCE: 2

Ala Ile Asn Gln Asp Gly Ser Glu Lys Tyr Tyr Val Gly Ser Val Lys
1               5                   10                  15

Gly

<210> SEQ ID NO 3
<211> LENGTH: 18
<212> TYPE: PRT
<213> ORGANISM: ARTIFICIAL
<220> FEATURE:
<223> OTHER INFORMATION: CDR3 = hypervariable region 3 of heavy chain of
      AIN457

<400> SEQUENCE: 3

Asp Tyr Tyr Asp Ile Leu Thr Asp Tyr Tyr Ile His Tyr Trp Tyr Phe
1               5                   10                  15

Asp Leu

<210> SEQ ID NO 4
<211> LENGTH: 12
<212> TYPE: PRT
<213> ORGANISM: ARTIFICIAL
<220> FEATURE:
<223> OTHER INFORMATION: CDR1' = hypervariable region 1 of light chain
      of AIN457

<400> SEQUENCE: 4

Arg Ala Ser Gln Ser Val Ser Ser Ser Tyr Leu Ala
1               5                   10

<210> SEQ ID NO 5
<211> LENGTH: 7
<212> TYPE: PRT
<213> ORGANISM: ARTIFICIAL
<220> FEATURE:
<223> OTHER INFORMATION: CDR2' = hypervariable region 2 of light chain
      AIN457

<400> SEQUENCE: 5

Gly Ala Ser Ser Arg Ala Thr
1               5

<210> SEQ ID NO 6
<211> LENGTH: 9
<212> TYPE: PRT
<213> ORGANISM: ARTIFICIAL
<220> FEATURE:
<223> OTHER INFORMATION: CDR3' = hypervariable region 3 of light chain
      AIN457

<400> SEQUENCE: 6

Gln Gln Tyr Gly Ser Ser Pro Cys Thr
1               5

<210> SEQ ID NO 7
<211> LENGTH: 381
<212> TYPE: DNA
<213> ORGANISM: HOMO SAPIENS
<220> FEATURE:
<221> NAME/KEY: CDS
<222> LOCATION: (1)..(381)

<400> SEQUENCE: 7
```

| | | |
|---|---|---|
| gag gtg cag ttg gtg gag tct ggg gga ggc ttg gtc cag cct ggg ggg<br>Glu Val Gln Leu Val Glu Ser Gly Gly Gly Leu Val Gln Pro Gly Gly<br>1               5                   10                  15 | | 48 |
| tcc ctg aga ctc tcc tgt gca gcc tct gga ttc acc ttt agt aac tat<br>Ser Leu Arg Leu Ser Cys Ala Ala Ser Gly Phe Thr Phe Ser Asn Tyr<br>            20                  25                  30 | | 96 |
| tgg atg aac tgg gtc cgc cag gct cca ggg aaa ggg ctg gag tgg gtg<br>Trp Met Asn Trp Val Arg Gln Ala Pro Gly Lys Gly Leu Glu Trp Val<br>        35                  40                  45 | | 144 |
| gcc gcc ata aac caa gat gga agt gag aaa tac tat gtg ggc tct gtg<br>Ala Ala Ile Asn Gln Asp Gly Ser Glu Lys Tyr Tyr Val Gly Ser Val<br>    50                  55                  60 | | 192 |
| aag ggc cga ttc acc atc tcc aga gac aac gcc aag aac tca ctg tat<br>Lys Gly Arg Phe Thr Ile Ser Arg Asp Asn Ala Lys Asn Ser Leu Tyr<br>65                  70                  75                  80 | | 240 |
| ctg caa atg aac agc ctg aga gtc gag gac acg gct gtg tat tac tgt<br>Leu Gln Met Asn Ser Leu Arg Val Glu Asp Thr Ala Val Tyr Tyr Cys<br>            85                  90                  95 | | 288 |
| gtg agg gac tat tac gat att ttg acc gat tat tac atc cac tat tgg<br>Val Arg Asp Tyr Tyr Asp Ile Leu Thr Asp Tyr Tyr Ile His Tyr Trp<br>        100                 105                 110 | | 336 |
| tac ttc gat ctc tgg ggc cgt ggc acc ctg gtc act gtc tcc tca<br>Tyr Phe Asp Leu Trp Gly Arg Gly Thr Leu Val Thr Val Ser Ser<br>    115                 120                 125 | | 381 |

<210> SEQ ID NO 8
<211> LENGTH: 127
<212> TYPE: PRT
<213> ORGANISM: HOMO SAPIENS

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
            85                  90                  95

Val Arg Asp Tyr Tyr Asp Ile Leu Thr Asp Tyr Tyr Ile His Tyr Trp
        100                 105                 110

Tyr Phe Asp Leu Trp Gly Arg Gly Thr Leu Val Thr Val Ser Ser
    115                 120                 125

<210> SEQ ID NO 9
<211> LENGTH: 327
<212> TYPE: DNA
<213> ORGANISM: HOMO SAPIENS
<220> FEATURE:
<221> NAME/KEY: CDS
<222> LOCATION: (1)..(327)

<400> SEQUENCE: 9

| | | |
|---|---|---|
| gaa att gtg ttg acg cag tct cca ggc acc ctg tct ttg tct cca ggg<br>Glu Ile Val Leu Thr Gln Ser Pro Gly Thr Leu Ser Leu Ser Pro Gly<br>1               5                   10                  15 | | 48 |

```
gaa aga gcc acc ctc tcc tgc agg gcc agt cag agt gtt agc agc agc        96
Glu Arg Ala Thr Leu Ser Cys Arg Ala Ser Gln Ser Val Ser Ser Ser
         20                  25                  30 tac tta gcc tgg tac cag cag aaa cct ggc cag gct ccc agg ctc ctc       144
Tyr Leu Ala Trp Tyr Gln Gln Lys Pro Gly Gln Ala Pro Arg Leu Leu
             35                  40                  45 atc tat ggt gca tcc agc agg gcc act ggc atc cca gac agg ttc agt       192
Ile Tyr Gly Ala Ser Ser Arg Ala Thr Gly Ile Pro Asp Arg Phe Ser
     50                  55                  60 ggc agt ggg tct ggg aca gac ttc act ctc acc atc agc aga ctg gag       240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agc tca ccg       288
Pro Glu Asp Phe Ala Val Tyr Tyr Cys Gln Gln Tyr Gly Ser Ser Pro
                 85                  90                  95 tgc acc ttc ggc caa ggg aca cga ctg gag att aaa cga                   327
Cys Thr Phe Gly Gln Gly Thr Arg Leu Glu Ile Lys Arg
             100                 105
```

<210> SEQ ID NO 10
<211> LENGTH: 109
<212> TYPE: PRT
<213> ORGANISM: HOMO SAPIENS

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Thr Phe Gly Gln Gly Thr Arg Leu Glu Ile Lys Arg
            100                 105

<210> SEQ ID NO 11
<211> LENGTH: 10
<212> TYPE: PRT
<213> ORGANISM: artificial
<220> FEATURE:
<223> OTHER INFORMATION: CDR1-x = hypervariable domain x of heavy chain
      of AIN457

<400> SEQUENCE: 11

Gly Phe Thr Phe Ser Asn Tyr Trp Met Asn
1               5                   10

<210> SEQ ID NO 12
<211> LENGTH: 11
<212> TYPE: PRT
<213> ORGANISM: artificial
<220> FEATURE:
<223> OTHER INFORMATION: CDR2-x = hypervariable domain of heavy chain x
      of AIN457

<400> SEQUENCE: 12

Ala Ile Asn Gln Asp Gly Ser Glu Lys Tyr Tyr

<210> SEQ ID NO 13
<211> LENGTH: 23
<212> TYPE: PRT
<213> ORGANISM: ARTIFICIAL
<220> FEATURE:
<223> OTHER INFORMATION: CDR3-x = hypervariable domain x of heavy chain
    AIN457

<400> SEQUENCE: 13

Cys Val Arg Asp Tyr Tyr Asp Ile Leu Thr Asp Tyr Tyr Ile His Tyr
1               5                   10                  15

Trp Tyr Phe Asp Leu Trp Gly
            20

<210> SEQ ID NO 14
<211> LENGTH: 215
<212> TYPE: PRT
<213> ORGANISM: homo sapiens

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 15
<211> LENGTH: 457
<212> TYPE: PRT
<213> ORGANISM: homo sapiens

<400> SEQUENCE: 15

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser Ala
        115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Arg
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430
```

```
Phe Ser Cys Ser Val Met His Glu Ala Leu His Asn His Tyr Thr Gln
        435                 440                 445

Lys Ser Leu Ser Leu Ser Pro Gly Lys
    450                 455
```